(12) United States Patent
Sun et al.

(10) Patent No.: US 11,719,632 B2
(45) Date of Patent: Aug. 8, 2023

(54) BIOMARKER DETECTION SYSTEM

(71) Applicants: Temasek Polytechnic, Singapore (SG); Agency for Science, Technology and Research, Singapore (SG); Tan Tock Seng Hospital Pte Ltd, Singapore (SG)

(72) Inventors: Ling Ling Sun, Singapore (SG); Willie Ng, Singapore (SG); Xiaodong Zhou, Singapore (SG); Ten It Wong, Singapore (SG); Yee Sin Leo, Singapore (SG)

(73) Assignees: Temasek Polytechnic, Singapore (SG); Agency for Science, Technology and Research, Singapore (SG); Tan Tock Seng Hospital Pte. Ltd., Singapore (SG)

( * ) Notice: Subject to any disclaimer, the term of this patent is extended or adjusted under 35 U.S.C. 154(b) by 16 days.

(21) Appl. No.: 16/318,946

(22) PCT Filed: Jul. 21, 2017

(86) PCT No.: PCT/SG2017/050372
§ 371 (c)(1),
(2) Date: Jan. 18, 2019

(87) PCT Pub. No.: WO2018/017021
PCT Pub. Date: Jan. 25, 2018

(65) Prior Publication Data
US 2019/0302022 A1 Oct. 3, 2019

(30) Foreign Application Priority Data
Jul. 21, 2016 (SG) .......................... 10201606001Q

(51) Int. Cl.
*G01N 33/543* (2006.01)
*G01N 21/552* (2014.01)
(Continued)

(52) U.S. Cl.
CPC ........... *G01N 21/554* (2013.01); *G01N 21/01* (2013.01); *G01N 21/648* (2013.01);
(Continued)

(58) Field of Classification Search
None
See application file for complete search history.

(56) References Cited

U.S. PATENT DOCUMENTS 7,738,096 B2 * 6/2010 Zhao .................... G01N 21/658
436/171
2015/0219643 A1 8/2015 Song et al.
(Continued)

FOREIGN PATENT DOCUMENTS

| CN | 101236208 A | 8/2008 |
| CN | 101438146 A | 5/2009 |

(Continued)

OTHER PUBLICATIONS

European Patent Office International Search Report dated May 18, 2018 in reference to co-pending International Application No. PCT/SG2017/050372 filed Jul. 21, 2017.
(Continued)

*Primary Examiner* — Melanie Brown
(74) *Attorney, Agent, or Firm* — Preston Smirman; Smirman IP Law, PLLC

(57) ABSTRACT

Disclosed is a localised surface plasmon resonance (LSPR) nanopillar assembly. The LSPR assembly is for use in sensing the presence of a biomarker when attached to a quantum dot. The LSPR assembly comprises a substrate and an array. The array comprises a LSPR nanopillar and a polymer spacer attached to the nanopillar. The LSPR assembly further comprises an antibody attached to the at least one polymer spacer. In the LSPR assembly, a combined height of the polymer spacer and antibody is selected by varying the
(Continued)

number of monomer units of the polymer spacer, so that, when in use with the biomarker and the quantum dot, the quantum dot is at a predetermined distance from the nanopillar.

8 Claims, 16 Drawing Sheets

(51) Int. Cl.
    *G01N 21/01*     (2006.01)
    *G01N 33/74*     (2006.01)
    *G01N 21/64*     (2006.01)

(52) U.S. Cl.
    CPC . *G01N 33/54353* (2013.01); *G01N 33/54373* (2013.01); *G01N 33/74* (2013.01); *G01N 2333/585* (2013.01)

(56) References Cited

U.S. PATENT DOCUMENTS

2016/0003817 A1* 1/2016 Chou ................ G01N 21/6486
                                                                        435/6.11
2018/0299458 A1* 10/2018 Gerion .................... B32B 15/02

FOREIGN PATENT DOCUMENTS

WO     2013154770 A1     10/2013
WO     2016064917 A1     4/2016

OTHER PUBLICATIONS

European Patent Office Written Opinion dated May 18, 2018 in reference to co-pending International Application No. PCT/SG2017/050372 filed Jul. 21, 2017.

Sun Ling Ling et al.; "Nanoimprinted Nanopillar Array Chip for Procalcitonin Detection" (Conference Presentation); Progress in Biomedical Optics and Imaging, SPIE—International Society for Optical Engineering, Bellinham, WA, US; vol. 9705; Mar. 24, 2016; pp. 97050T-97050T.

Vamsi K. K. et al.; "Interaction of surface plasmons with CdTe quantum dot excitons"; Proc. of SPIE vol. 5955; Metamaterials; vol. 5955; Sep. 28, 2005; pp. 59550L1-59550L-6.

Chinese Office Action dated Jun. 25, 2021 in co-pending Chinese Patent Application No. 201780045273X.

* cited by examiner (a) Side View  (b) Top View

BIOMARKER DETECTION SYSTEM

FIELD

The present disclosure relates to a biomarker detection system and its components, its use thereof and a method of detecting a biomarker. In particular, the present disclosure relates to a nanopillar assembly, a chip comprising such an assembly, and a system employing the chip in the detection of the biomarker.

BACKGROUND

Sepsis results from the over response of human immunosystem to infection, and might cause death by tissue hypoperfusion, organ dysfunction, or hypotension. Every two minutes in US, there is a death caused by sepsis, its death toll of 258,000 per year is higher than the sum of prostate cancer, breast cancer and acquired immune deficiency syndrome (AIDS). In Singapore, 17% of the total death is due to sepsis. Globally, it causes more than 8 million deaths annually. However, about 80% of the mortality from sepsis could be prevented through on time diagnosis, and each hour of delay on treatment will increase the mortality up to 8%. Currently, the "gold standard" for diagnosis of sepsis is blood cultures. However, the issues with running a blood culture for the detection of sepsis is that it takes about 2-3 days to run the test and require a large amount of blood sample. Additionally, the accuracy of this test is not high: the rate of false positive is about 30% and for false negative is about 50%.

Biomarkers are being investigated as an alternative for sepsis diagnosis. Procalcitonin (PCT) is identified as an early and highly specific biomarker in response to bacterial infection. PCT is a 116 amino-acid peptide serves as the precursor of the hormone calcitonin. In the blood stream of healthy individuals, the level of PCT is below 0.05 ng/ml. It rises within 2-4 hours after onset of a bacterial infection and falls rapidly as the infection resolves. The magnitude and duration of PCT elevation correlate with infection severity and prognosis. In early stages of sepsis, the PCT level is generally greater than 0.5-2 ng/ml. As sepsis develops, PCT value can reach between 10 and 100 ng/ml, or considerably higher in individual cases. This enables diagnostic differentiation between these various clinical conditions and a severe bacterial infection (sepsis). It is noted that the PCT values of <1 ng/mL and 1 mg/mL correspond to 10-12% and 96% likelihood of septic patients.

Current technologies for PCT detection are limited. Only the immunosystems SIEMENS ADVIA Centaur XP and ADVIA Centaur CP based on chemiluminescent immunoassay (CLIA) and Roche Diagnostics cobas e601, e602 and e411 immunosystems based on two-step two-site sandwich electro-chemiluminescence immunoassay (ECLIA) can run PCT assays. The disadvantages of such an immunosystem are its bulky size, cost and trained, professional operators are required. The bulkiness of these systems means that they are not portable and convenient to use, especially in primary care applications and at rural areas where the demand is the greatest. Running these assays is also a highly labour intensive process, with long incubation periods (about 2 h) and expensive.

As an example, Tan Tock Seng Hospital has been using the automated Roche Diagnostics cobas e 601 for several years. In addition to the assay time, the actual turn-around-time from sample to result may be several hours to days as the tests are lab-based. Currently the test machines are bulky and expensive, and require professional technical expertise to operate in centralized test centre only.

As such, there is a need for near physician, on time detection of PCT.

It is generally desirable to develop a highly sensitive and selective system for PCT detections in clinics, emergency departments and on the wards to enable doctors to make critical decisions in a clinical relevant timely manner.

It is generally desirable to overcome or ameliorate one or more of the above mentioned difficulties, or at least provide a useful alternative.

SUMMARY

The present inventors identified the potential for localized surface plasmon resonance (LSPR) based biosensors in the detection of biomarkers. LSPR biosensors have offered rapid detection and are simple-to-operate. LSPR is generated on metal nanostructures upon the illumination of light whose energy can be absorbed by the nanostructures and cause collective electron charge oscillations on its surface.

The inventors attempted to detect the presence of a biomarker using LSPR by detecting the shift of the LSPR absorption due to the refractive index change upon molecule binding. Against the gold standard, the sensitivity of this LSPR technique was too low and suggested that LSPR was not going to be capable of yielding medically acceptable results.

The inventors nevertheless developed a method using LSPR to excite fluorescent labels in a sandwich assay. As a light interacts with the nanostructures, LSPR is generated and the nanostructures serve as optical nano-antennas to trap the light nearby their surface where the light intensity will be 10-100 times more concentrated. However, the inventors found with this technique that strong LSPR quenched the fluorescence of the labels when those labels were too close to the nanostructures.

In both these methods, either a confocal microscope or a high-end expensive fluorescent microscope was used for the detection of the biomarkers with LSPR enhanced fluorescent signal. Such instruments are expensive and bulky.

In an aspect, the present invention provides a localised surface plasmon resonance (LSPR) nanopillar assembly for use in sensing the presence of a biomarker when attached to a quantum dot, comprising:
a) a substrate;
b) an array comprising:
  i) a LSPR nanopillar; and
  ii) a polymer spacer attached to the nanopillar; and
c) an antibody attached to the at least one polymer spacer; and
wherein a combined height of the polymer spacer and antibody is selected by varying the number of monomer units of the polymer spacer, so that, when in use with the biomarker and the quantum dot, the quantum dot is at a predetermined distance from the nanopillar.

In another aspect, the present invention provides a LSPR nanopillar assembly wherein the combined height is selected so that, when in use, the quantum dot is within a LSPR region dictated by dimensions of the nanopillar.

In another aspect, the present invention provides a LSPR fluidic chip comprising:
a) an inlet;
b) an outlet;
c) a channel connecting the inlet and the outlet; and
d) a LSPR nanopillar assembly in fluid communication with the channel between the inlet and the outlet;

wherein the LSPR nanopillar assembly for use in sensing the presence of a biomarker when attached to a quantum dot, comprises:
  i) a substrate;
  ii) an array comprising:
    (i) a LSPR nanopillar; and
    (ii) a polymer spacer attached to the nanopillar; and
  iii) an antibody attached to the at least one polymer spacer; and
wherein a combined height of the polymer spacer and antibody is selected by varying the number of monomer units of the polymer spacer, so that, when in use with the biomarker and the quantum dot, the quantum dot is at a predetermined distance from the nanopillar.

In another aspect, the present invention provides a valve assembly comprising:
a) a holder;
b) at least three valve supports in the holder; and
c) at least one solution reservoir cavity per valve support, each solution reservoir cavity being disposed in the holder; wherein the valve supports are arranged substantially in a circle about a fixed point of the holder, and wherein the solution reservoir cavities are positioned substantially circumferentially to the valve supports.

In another aspect, the present invention provides a LSPR biomarker detection system for use in sensing a biomarker when attached to a quantum dot, comprising:
a) a first solution reservoir containing a biomarker sample;
b) a second solution reservoir containing a further biomarker antibody;
c) a third solution reservoir containing a quantum dot modified to attach to the biomarker antibody;
d) a LSPR fluidic chip support adapted to receive a LSPR fluidic chip, comprising:
  i) an inlet connector for connecting to an inlet of the LSPR fluidic chip; and
  ii) an outlet connector for connecting to an outlet of the LSPR fluidic chip, the LSPR fluidic chip comprising a channel connecting the inlet and the outlet, and a LSPR nanopillar assembly in fluid communication with the channel between the inlet and the outlet, the nanopillar assembly being a nanopillar assembly as defined herein;
e) a flow mechanism comprising a pump system selectively in fluid communication with the inlet connector of the LSPR fluidic chip support, the flow mechanism being for dispensing contents of the first solution reservoir, second solution reservoir and third solution reservoir into the LSPR fluidic chip via the inlet connector;
f) a valve assembly disposed between the flow mechanism and the LSPR fluidic chip support, comprising an open state and a closed state for each of the first solution reservoir, second solution reservoir and third solution reservoir wherein, in the open state, the respective first, second or third reservoir is in fluid communication with the LSPR fluidic chip support and, in the closed state, the respective first, second or third reservoir is not in fluid communication with the LSPR fluidic chip support;
g) a light source for directing a source electromagnetic wave through the LSPR fluidic chip;
h) a detection mechanism comprising a photodetector for detecting an emitted electromagnetic wave originating from the quantum dot; and
i) a controller for operating the flow mechanism, valve assembly, light source and detection mechanism, to sequentially dispense the biomarker sample, biomarker antibody and quantum dot through the inlet connector, activate and deactivate the light source and detection mechanism.

In an embodiment, the present invention provides a biomarker detection system as described herein, wherein the biomarker is procalcitonin.

In another embodiment, the present invention provides a biomarker detection system as described herein, wherein the biomarker detection system is procalcitonin detection system.

In another aspect, the present invention provides a method for detecting a biomarker in a sample, comprising:
a) selecting a polymer spacer;
b) attaching the polymer spacer to a nanopillar;
c) attaching a biomarker antibody to the polymer spacer, the polymer spacer being selected so to have a specific number of monomer units so that a combined height of the polymer spacer and biomarker antibody, when in use with a biomarker and a quantum dot, positions the quantum dot at a predetermined distance from the nanopillar;
d) contacting the biomarker to the biomarker antibody;
e) contacting a further biomarker antibody to the biomarker;
f) attaching the quantum dot to the further biomarker antibody;
g) directing a source electromagnetic wave through the nanopillar; and
h) detecting an intensity of an emitted electromagnetic wave originating from the quantum dot.

In the assembly described herein, the ability to tune or determine a combined, total length of the polymer spacer and biomarker ensures the quantum dot is positioned a predetermined distance from the nanopillar surface. In view of the following disclosure, it will become apparent that the "predetermined distance" will depend on the dimensions of the nanopillar (which defines a region of high electron density or a LSPR region).

BRIEF DESCRIPTION OF THE DRAWINGS

Some embodiments of the present invention will now be described by way of non-limiting example only, with reference to the accompanying drawings in which.

DETAILED DESCRIPTION OF THE INVENTION

Figure 1:
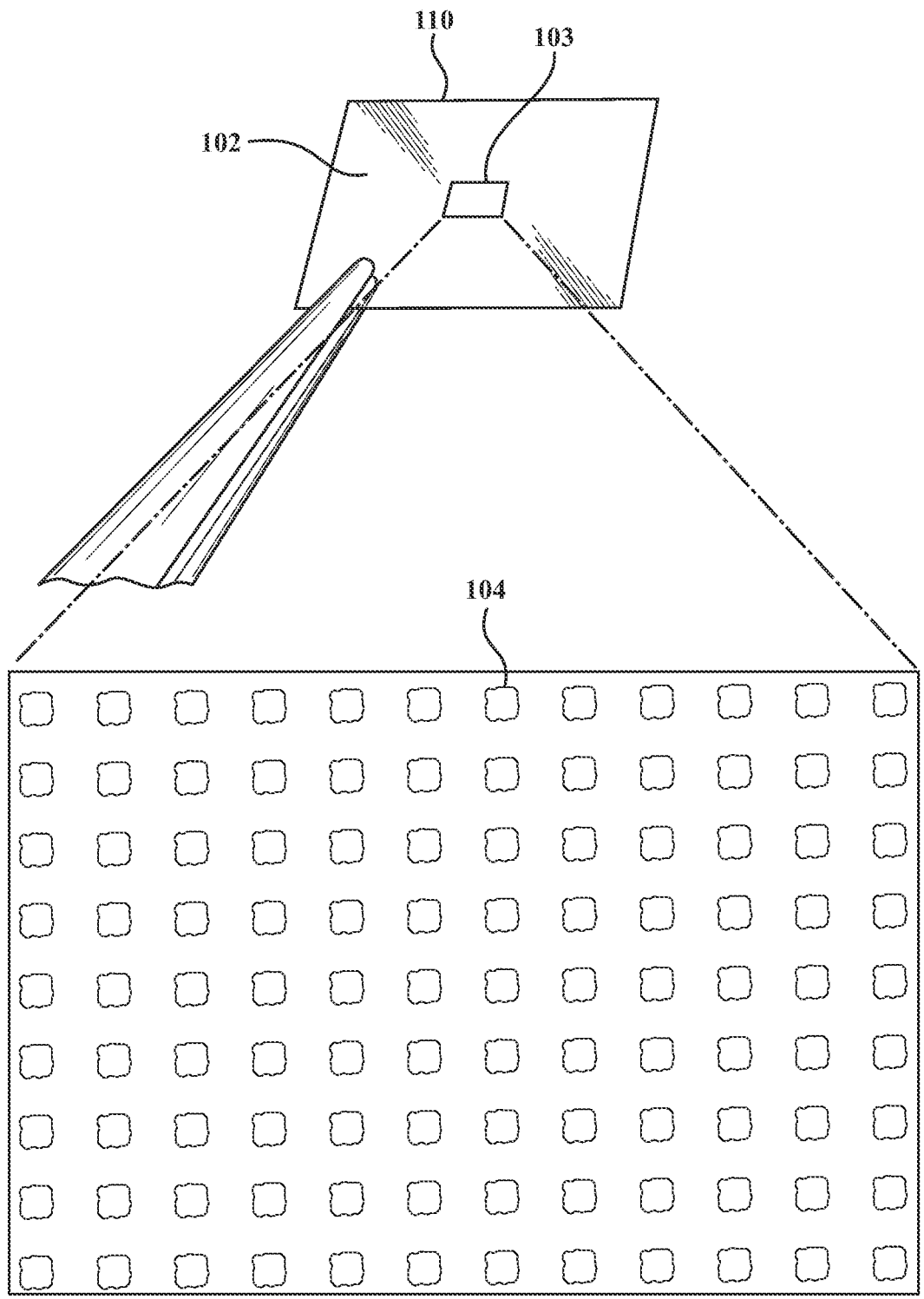
FIG. 1 shows an example of a LSPR nanopillar assembly 110.

The present invention relates to a localised surface plasmon resonance (LSPR) nanopillar assembly, a LSPR fluidic chip, a valve assembly and a biomarker detection system. Additionally, the present invention relates to a method of detecting a biomarker. In particular, embodiments of the present invention may be useful for procalcitonin (PCT) detection.

The term "localised surface plasmon resonance" or "LSPR" is intended to include within its scope a coherent, collective spatial oscillation of the conduction electrons in a metallic nanosurface. This oscillation can be excited by electromagnetic wave. LSPR structures exhibit enhanced near-field amplitude at the resonance wavelength. This field is highly localized at a nanosurface and decays rapidly away from the nanosurface/dielectric interface into a dielectric background. Localization means the LSPR has very high spatial resolution.

The term "PEG" or "polyethylene glycol" refers to poly(ethylene oxide) of any chain length, PEG has a molecular structure built up mainly or completely from a number of ethylene oxide monomers covalently bonded together. For example, PEG with two monomer units of ethylene oxide is referred to $PEG_2$. For example, PEG with three monomer units of ethylene oxide is referred to $PEG_3$. PEG can be, but not limited to, of a linear structure, branch structure, crosslinked or dendritic. PEG also include all types of co-polymers, with a monomer being at least ethylene oxide. Such co-polymers include alternating co-polymer, random co-polymer, block co-polymer, graft co-polymer and the like. The terminal ends of the PEG polymer may be modified with any functionality. The terminal ends of the PEG may have the same functionality at all ends of the polymer or only at selected ends. For example, linear PEG may have the same functionality at both ends of the chain or each end has different functionality. The terminal moiety can be, but not limited to, hydroxyl, thiol, carboxylic acid, amine, or any protecting group.

The term "quantum dot" is used in the broadest sense and includes all types of semiconductor nanoparticles. Many types of quantum dot will emit light of specific frequencies if electricity or light is applied to them, and these frequencies can be precisely tuned by changing the dots' size, shape and material, giving rise to many applications. As such, as used herein, quantum dots can refer to nanomaterials having the size from 0.1 nm to 999 nm. As used herein, quantum dotes can refer to nanomaterials having different shapes such as, but not limited to, spheres, cubes, rods, pyramids, cone, cylinder, tetrahedron, triangular prism, icosahedron, octadedron, dodecahedron, hexagonal prism, ellipsoid, pentagonal prism, pentagonal pyramid, hexagonal pyramid or octagonal prism. As used herein, quantum dots can refer to nanomaterials made from different semiconductors and its combination with other elements, such as, but not limited to, Cd, Se, S, Zn, Te, Au, Ag, Ga, P, Al, Sb, As, In, Si, Sb or Ge.

The term "biomarker" is used in the broadest sense and refers to a subcategory of medical signs which can be measured accurately and reproducibly. It can be any substance, structure, or process that can be measured in the body or its products and influence or predict the incidence of outcome or disease. Thus, it can refer to a naturally occurring molecule, gene or characteristic by which a particular pathological or physiological process, disease can be identified. It includes almost any measurement reflecting an interaction between a biological system and a potential hazard, which may be chemical, physical, or biological. The measured response may be functional and physiological, biochemical at the cellular level, or a molecular interaction. It is an objective, quantifiable characteristics of biological processes, which may but do not necessarily correlate with a patient's experience and sense of wellbeing. The biomarker used in some of the embodiments discussed below is procalcitonin, thus making the biomarker detection system of the present disclosure a procalcitonin detection system.

The term "antibody" or "ab" is used in the broadest sense and include monoclonal antibodies, isolated, engineered or recombinant antibodies (e.g., full length or intact monoclonal antibodies), polyclonal antibodies, multivalent antibodies or multispecific antibodies (e.g., bispecific antibodies) and also antibody fragment thereof, so long as they exhibit the desired biological activity. An "antibody fragment" or "antigen-binding fragment" comprise a portion of an intact antibody comprising the antigen-binding or variable region thereof. Examples of antibody fragments include Fab, Fab', $F(ab')_2$, and Fv fragments; diabodies; linear antibodies; single-chain antibody molecules; bispecific and multispecific antibodies formed from antibody fragment(s). An "isolated antibody", as used herein, is intended to refer to an antibody that is substantially free of other antibodies having different antigenic specificities (e.g., an isolated antibody that specifically binds epidermal growth factor receptor (EGFR) is substantially free of antibodies that specifically bind antigens other than EGFR). An isolated antibody that specifically binds e.g. EGFR may, however, have cross-reactivity to other antigens, such as EGFR molecules from other species. Moreover, an isolated antibody may be substantially free of other cellular material and/or chemicals. More particularly, such a molecule consists of a glycoprotein comprising at least two heavy (H) chains and two light (L) chains inter-connected by disulfide bonds. Each heavy chain comprises a heavy chain variable region (or domain) (abbreviated herein as HCVR or VH) and a heavy chain constant region. The heavy chain constant region comprises three domains, CHI, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (C1q) of the classical complement system.

The antibody may be conjugated to suitable polymers via cysteine or lysine residues present on the antibody. The antibody may also be engineered to have a specific number of cysteine or lysine residues for conjugation to suitable polymers. The antibody may also be engineered at specific sites to incorporate unnatural amino acids or to introduce functional groups to specific amino acids to allow linkers to be attached to the antibody.

Figure 2:
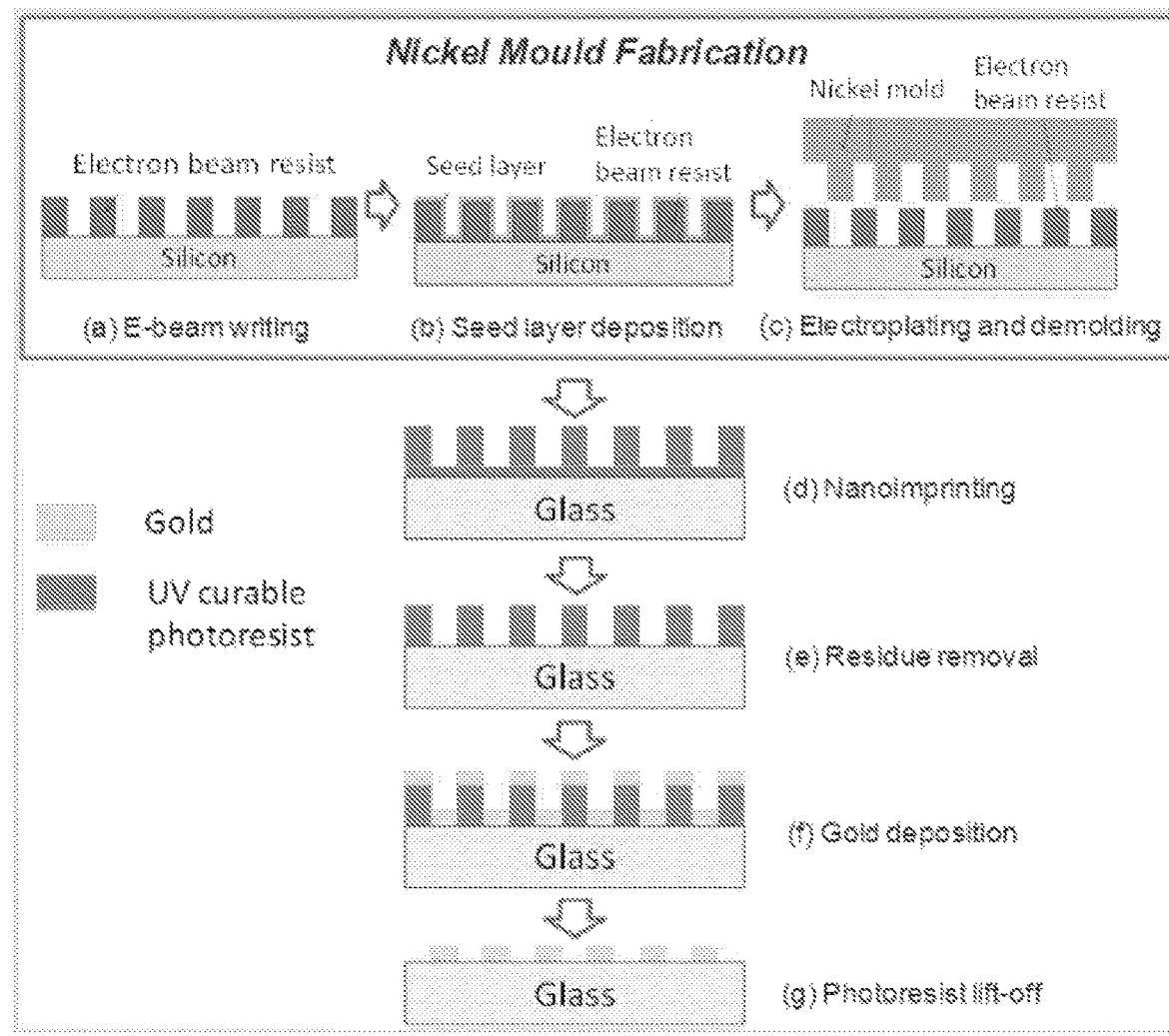
FIG. 2 illustrates a fabrication method of nanopillar assembly 110.

In an aspect, the present invention provides a LSPR nanopillar assembly 110. FIG. 1 shows an example of a LSPR nanopillar assembly 110. The LSPR nanopillar assembly 110 is adapted for use in sensing the presence of a biomarker when attached to a quantum dot. The LSPR assembly 110 comprises a substrate 102 and an array 103. The substrate 102 supports the nanopillar array 103. The substrate 102 can be fabricated by mass fabrication as shown in FIG. 2 and described below. For example, nanoimprinting on wafer can be used.

The array 103 comprises a LSPR nanopillar 104—in other words at least one nanopillar 104 and, presently, a plurality of nanopillars 104—and a polymer spacer 106 attached to the nanopillar 104. The array 103 is used in enhancing LSPR developed by an incident electromagnetic wave such as a photon.

Figure 3:
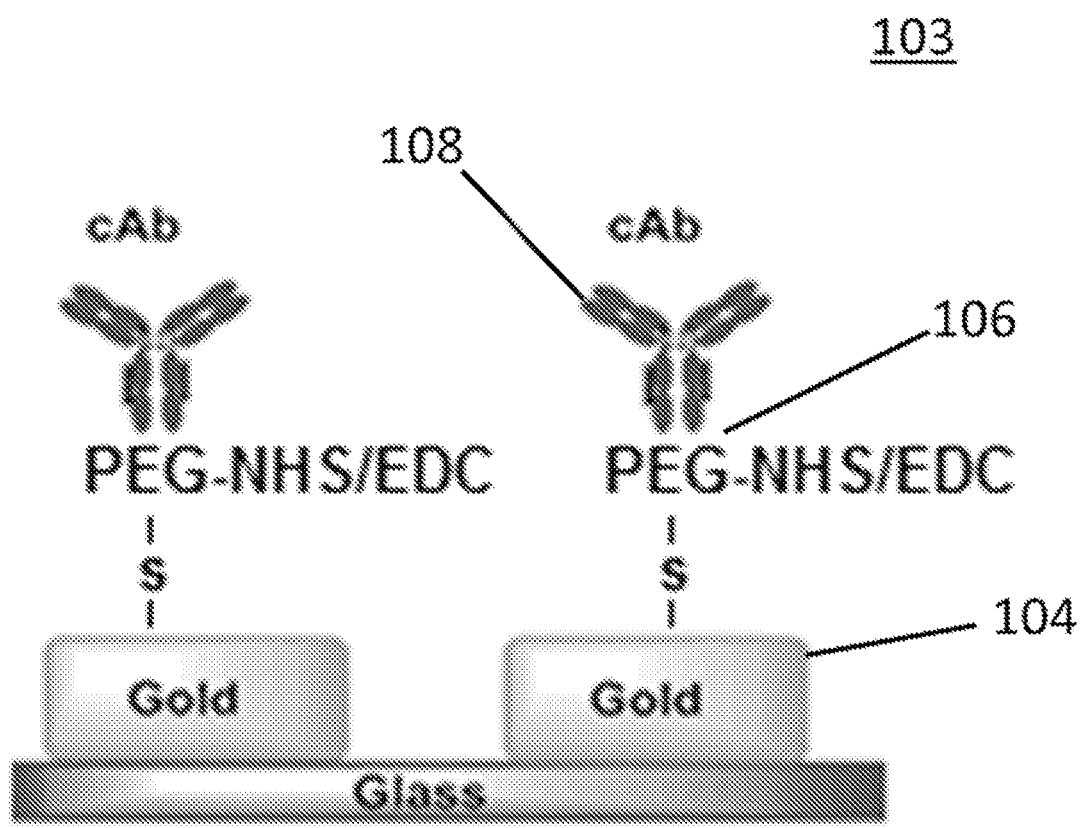
FIG. 3 shows an illustration of an array 103.

The LSPR assembly 110 further comprises an antibody 108 (as shown in FIG. 3) attached to the polymer spacer 106. Importantly, the combined height of the polymer spacer 106 and antibody 108 is selected by varying the number of monomer units of the polymer spacer 106. This facilitates positioning of a quantum dot 500 (see FIG. 7) at a predetermined distance from the nanopillar when the LSPR assembly 110 is in use.

The nanopillar assembly 110 can be fabricated by mass fabrication. For example, nanoimprinting on wafer can be used. FIG. 2 shows an example of how this can be done.

FIG. 1 shows a substrate 102 of dimensions 1 cm×1 cm with the central 0.9 mm×0.9 mm area covered by nanopillars 104. The nanopillars are arranged in an array with a pitch of about 320 nm, size of about 140 nm×about 140 nm and height of about 55 nm. The metal layer includes about 5 nm of chromium as the adhesive layer and about 50 nm of gold.

The size of the substrate can be chosen to fit a particular chip design, or to support a nanopillar array of a particular size, where the size of the nanopillar array may be selected depending on the desired sensitivity of the assay, the size of the biomarker sample and so forth. In some embodiments, the substrate 102 is about 1.5 cm long by about 1.5 cm wide (i.e. 1.5 cm×1.5 cm), but it may alternatively be any other desired dimensions such as about 1.4 cm×1.4 cm, about 1.3 cm×1.3 cm, about 1.2 cm×1.2 cm, about 1.1 cm×1.1 cm, about 1.0 cm×1.0 cm, about 0.9 cm×0.9 cm, about 0.8 cm s 0.8 cm, about 0.7 cm×0.7 cm, about 0.6 cm×0.6 cm, about 0.5 cm×0.5 cm, of a non-square shape (e.g. 1.4 cm×1.5 cm) or any other appropriate dimensions and shape.

The size of the nanopillar assembly 110 may be substantially the same as the size of the substrate 102, or may exceed the size of the substrate 102 where the substrate 102 is mounted on, for example, a light transmissive layer.

As mentioned above, the size of the nanopillar array can be selected to suit a desired sensitivity (e.g. larger array provides more sites for attachment of the biomarker and thus can increase sensitivity), and to produce an array with a desired number of nanopillars and pitch (i.e. distance between centers of neighbouring nanopillars). The LSPR nanopillar 104 may, for example, be arranged in an array about 1.5 mm long by about 1.5 mm wide, about 1.0 mm long by about 1.0 mm wide, 0.8 mm long by about 0.8 mm wide or any other desired dimensions.

The substrate 102 having LSPR nanopillars 104 may be a material suitable for mass fabrication. In an embodiment, silicon substrate is used. In another embodiment, glass substrate is used. In another embodiment, fused silica substrate may be used. In another embodiment, nickel substrate may be used. In another embodiment, polymer substrate may be used. In another embodiment, polydimethylsiloxane substrate may be used.

Array 103 can comprise one or more nanopillars 104. As shown in FIG. 1, array 103 can comprise nanopillars of equal size and shape, equally spaced throughout. In other embodiments, the nanopillars may be one or more of:
not substantially equal in size and shape;
not equally spaced throughout;
substantially equal in size but not shape;
substantially equal in shape but not size;
randomly or non-uniformly spaced;
substantially gradiently spaced so between a region of high nanopillar density to a region of lower nanopillar density; and
any other suitable design of nanopillars.

In general, the nanopillar dimensions, shape and spacing may be selected to maintain an electron dense region, or LSPR region, of a desired size or shape.

FIG. 3 shows an illustration of an array 103, comprising LSPR nanopillar 104, a polymer spacer 106 attached to the nanopillar 104 and an antibody 108 attached to the at least one polymer spacer 106. One or more polymer spacers can be attached to each nanopillar. Often, there will be a plurality of polymer spacers attached to each nanopillar surface. Once polymer spacer has been attached to the nanopillar, the polymer spacer is attached to the antibody. One or more antibodies can be attached to each polymer spacer. Notably, in practice there may not be a one-to-one correlation between polymer spacers and antibodies. Instead, multiple polymer spacers may attach to a single antibody. Also, some polymer spacers may not ultimately attach to an antibody—this is particularly the cases where, for example, the biomarker sample is low in the biomarker, or does not contain it (e.g. the patient from whom the sample was derived did not have the expected condition), and where the biomarker is large when compared with the size of the spacer such that a single biomarker attached to a nearby spacer will effectively preclude another single biomarker from attaching to a nearby, as yet unattached, polymer spacer. Upon attachment to the spacer, the antibody is indirectly attached to the nanopillar. One or more antibodies can be indirectly attached to a single nanopillar.

Without wanting to be bound by theory, it is believed that the interaction between light and metal nanostructure can generate LSPR. LSPR of metal nanostructures redistributes the electromagnetic field energy. At the resonance wavelength, the light is absorbed and focused at the corners of the metal nanostructures. As such, the metal nanostructures act like antennae. In the present invention, the top of the nanopillar can act as a hotspot for LSPR. When the nanopillar is used with quantum dots, the fluorescence (emitted electromagnetic wave) of quantum dots may be enhanced by coupling with the LSPR. To obtain the brightest fluorescence signal from the quantum dot, the LSPR should be about 40-120 meV higher in energy than the quantum dot emission peak. Additionally, the plasmonic spectral shape should coincide with the quantum dot's excitation spectrum. Metal nanopillars have a well-controlled plasmon peak and narrower band. As such, nanopillars may be used to enhance the fluorescence signal of quantum dots for biomarker detection. With LSPR enhanced fluorescence signal, better sensitivity and/or detection may be achieved.

However, not all nanostructured surfaces that are able to generate LSPR are suitable for the present invention. In particular, it was found that using nanoholes resulted in much lower enhancement of the quantum dot fluorescence when compared with the strategy ultimately taken by the inventors, in employing a nanopillar and spacer arrangement.

The quantum dot 500, when in use with the biomarker, can be tuned to be at a predetermined distance from the nanopillar 104. One way is by varying the polymer spacer 106 length. The polymer spacer length can be varied by changing the number of monomer units in the polymer spacer. In this way, the combined height of the polymer spacer and antibody can be selected such that when the quantum dot 500 attaches, the distance of the quantum dot 500 to the nanopillar 104 can be predetermined. This tuning of the distance allows the quantum dot 500 to be in a favourable region of the LSPR density. By doing so, the quantum dot 500 is in a favourable position for enhancement of its fluorescence by LSPR.

In view of the present disclosure, it will be appreciated that a "predetermined distance" of the quantum dot from the nanopillar is variable yet 'predetermined' to the extent that the quantum dot is positioned with sufficient accuracy (e.g. within a desired region in the LSPR region of the nanopillar) that it will be detectably excited upon the corresponding nanopillar experiencing LSPR (i.e. an emission electromagnetic wave, or photon, will be generated by the quantum dot and will be detectable). The combined height may thus be dependent on the dimensions of the nanopillar, which can affect the size and shape of the LSPR region. The combined height may similarly be dependent on the size of the antibody attached to the biomarker after the biomarker sample is flowed over the nanopillar assembly, and also on the size of the (functionalised) quantum dot.

The number of monomer units in the spacer 106 may be selected as needed to achieve a desired combined height of the spacer 106 and antibody 108, thereby to position the quantum dot 500 in the LSPR region of the nanopillar. The polymer spacer may have, for example, about 2 monomer units, about 3 monomer units, about 4, 5, 6, 7, 8, 9, 10, 15, 20, 50, 75, 100, 10,000 monomer units and so on, as needed. The term "about" in this context indicates that while a particular number of monomer units is desired, the fabrication of the spacer may yield slight variations in that number, in a Gaussian distribution about the ideal or desired number of monomer units. For clarity, the word "about" may be omitted without loss of generality, and the same distribution will be expected to apply (e.g. "3 monomer units" means "about 3 monomer units").

In an embodiment, the combined height of the polymer spacer 106 and antibody 108 is in the range of 10-200 nm. The combined height may alternatively be in the range of 10-180 nm, 10-160 nm, 15-140 nm, 20-120 nm, 25-100 nm, 30-90 nm, 35-80 nm, 40-80 nm, 45-70 nm, 50-60 nm or another desired combined height.

The enhancement factor, as used herein, is the ratio of the emitted light intensity in the presence of nanopillars with respect to the emitted light intensity in the absence of nanopillars. The enhancement factor is thus dependent on the LSPR overlap with the excitation and emission wavelength of the quantum dot. The enhancement factor can be adjusted by, for example, varying the dimensions of the nanopillars in the array, changing their shape, or the distance of the quantum dot from the nanopillars. For example, an enhancement factor of about 10-100 may be achieved. The enhancement factor may alternatively be in the range of about 15-90, about 20-80, or any other desired ranges. The enhancement factor may be about 10, about 15, about 20, about 25, about 30, about 40, about 50, about 60, about 70, about 80, about 90, about 100, or another desired value. For example, nanopillars may achieve an enhancement factor of at least 24.

The method for attaching the spacer to the nanopillar is selected, for example, to maintain the spacer in an upright orientation—in other words, the spacer projects substantially directly upwardly from, or normal to, the surface of the nanopillar to which it is attached. In some embodiments, the LSPR nanopillar assembly 110 comprises of the polymer spacer 106 conjugated to the nanopillar 104. The antibody may similarly be conjugated to the polymer spacer. In a similar manner, through the use of specific chemical interactions, the antibody may likewise be oriented in an upright position to receive the biomarker. In other embodiments, the polymer spacer is chemically bonded (covalent) to both the nanopillar and the antibody. In another embodiment, the polymer spacer is physically attached to the nanopillar, and may be similarly physically attached to the antibody. Examples of physical bonds include, but not limited to, electrostatic interactions, hydrophobic interactions, hydrophilic interactions, hydrogen bonding and non-covalent biological interactions.

In some embodiments, the polymer spacer 106 is a linear polymer spacer. This ensures a highly accurate position of the end of the polymer spacer opposite the end of the polymer spacer attached to the nanopillar. The linear polymer spacer can comprise two opposed terminal ends. One terminal end can be attached to the nanopillar and the other terminal end can be attached to the antibody. In another embodiment, the polymer spacer is a non-linear polymer spacer. Non-linear polymer spacers can include branched polymers, dendrimers and the like. The non-linear polymer spacer can comprise three or more terminal ends. At least one of the terminal ends can be attached to the nanopillar and one or more of the remaining terminal ends can be attached to the antibody.

In some embodiments, the polymer spacer 106 is conjugated to the nanopillar 104 by a sulphide bond. This ensures a stronger bond that would be achieved by, for example, physical bonding. In another embodiment, the conjugation is by an oxo bond. In another embodiment, the conjugation is by a silica bond. In another embodiment, the conjugation is by a siloxane bond. In another embodiment, the conjugation is by a silicon bond (eutectic). Other types of conjugation methods known in the art are also included herein.

The polymer spacer 106 may be similarly conjugated to the antibody 108 by an amide bond. In another embodiment, the conjugation is by an ester bond. In another embodiment, the conjugation is by an ether bond. In another embodiment, the conjugation is by a sulphide bond. In another embodiment, the conjugation is by a siloxane bond. In another embodiment, the polymer spacer is attached to the antibody by non-covalent interaction. In another embodiment, the attachment is by non-covalent biological interaction. In another embodiment, the attachment is by biotin streptavidin interaction. In another embodiment, the attachment is by biotin avidin interaction. Other types of attachment methods known in the art is also included herein.

In some embodiments, the polymer spacer 106 is a polyethylene glycol (PEG) spacer. The polymer spacer may alternatively be one of the following:
 a hydrophilic polymer spacer;
 a polyelectrolyte spacer;
 a polyanion spacer or a polycation spacer—examples of polyelectrolytes are polyacrylic acid, polyallylamine and the like;

a polyol spacer;

a hydrophobic polymer spacer such as polyethylene;

a peptide spacer;

a polynucleic acid spacer such as DNA or RNA;

a phospholipid; and a mixture of spacer types.

The PEG spacer may be selected to have 3-100 monomer units, about 100 monomer units, about 75 monomer units, about 50 monomer units, about 20 monomer units, about 10 monomer units, about 9, 8, 7, 6, 5, 4 or 3 monomer units as desired.

The array 103 can comprise a monolayer of polymer spacer 106 attached to the nanopillar 104. A monolayer means that the polymer spacer region is one molecule thick. The monolayer also means that there is a packing order, or mutual alignment, to the polymer spacer. This monolayer may be a monolayer of peptide, a monolayer of polynucleic acid, a monolayer of phospholipid or another monolayer as desired.

Without wanting to be bound by theory, it is believed that the LSPR region can be dictated by the dimensions of the nanopillar 104. By varying the dimensions of nanopillar 110, the resonance wavelength can be changed. The LSPR spatial volume can also be affected. As such, the LSPR region can be tuned. The length and width of the nanopillar 104 can be individually tuned to for a favourable LSPR region. The pitch of the nanopillar 104 influences the distribution of LSPR regions and hence a detectable signal. In an embodiment, the combined height of the polymer spacer 106 and the antibody 108 is selected so that, when in use, the quantum dot 500 is within a LSPR region dictated by dimensions of the nanopillar 104. In another embodiment, the combined height is selected so that the quantum dot 500 is in a favourable location of the LSPR region. In another embodiment, the combined height is selected so that quantum dot 500 is in a LSPR region for a fluorescence enhancement factor of about 10-100.

In some embodiments, the nanopillar 104 has a length of about 50 nm to about 250 nm. The nanopillar may alternatively have a length of about 50 nm, about 60 nm, about 80 nm, about 100 nm, about 120 nm, about 140 nm, about 160 nm, about 180 nm, about 200 nm, about 220 nm, about 240 nm, about 250 nm or any other length.

In some embodiments, the nanopillar 104 has a width of about 50 nm to about 250 nm. The nanopillar may alternatively have a width of about 50 nm, about 60 nm, about 80 nm, about 100 nm, about 120 nm, about 140 nm, about 160 nm, about 180 nm, about 200 nm, about 220 nm, about 240 nm, about 250 nm or any other width.

In some embodiments, the nanopillar 104 has a height of about 20 nm to about 100 nm. The nanopillar may alternatively have a height of about 20 nm, about 30 nm, about 40 nm, about 45 nm, about 50 nm, about 55 nm, about 60 nm, about 65 nm, about 70 nm, about 80 nm, about 90 nm, about 100 nm or any other height.

In some embodiments, the nanopillar array comprises a plurality of nanopillars. The pitch is the distance between the nanopillars, calculated from the center of a nanopillar to the center of an adjacent nanopillar. The pitch of the nanopillar array may be about 150 nm to about 500 nm, or about 150 nm. The pitch may alternatively be about 160 nm, about 180 nm, about 200 nm, about 220 nm, about 240 nm, about 260 nm, about 280 nm, about 300 nm, about 320 nm, about 340 nm, about 360 nm, about 380 nm, about 400 nm, about 420 nm, about 440 nm, about 460 nm, about 480 nm or about 500 nm.

In some embodiments, the nanopillar 104 is a gold nanopillar. In other embodiments, the nanopillar is a silver nanopillar.

Figure 4:
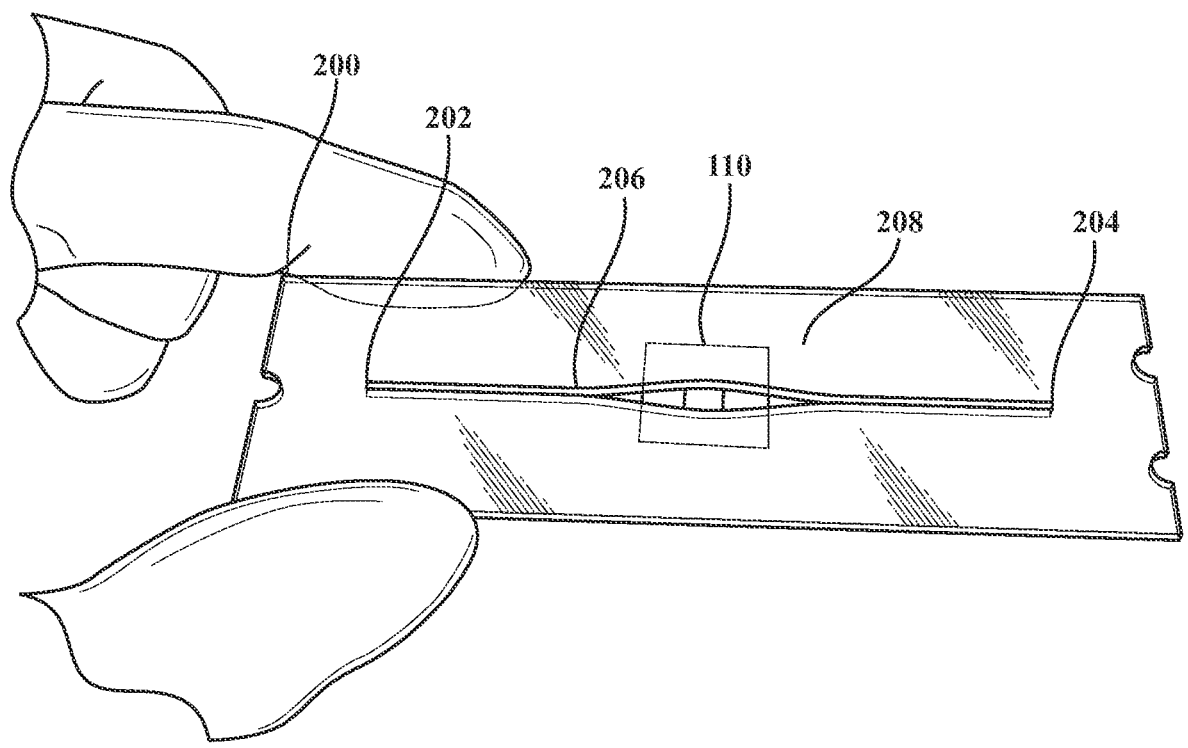
FIG. 4 shows an example of a LSPR fluidic chip 200.

The present invention also discloses a LSPR fluidic chip 200. FIG. 4 shows an example of a LSPR fluidic chip 200. Chip 200 is fabricated to integrate with nanopillar assembly 110 for liquid bio-reagents and buffer solutions delivery and processing. Chip 200 comprises an inlet 202, an outlet 204, a channel connecting the inlet and the outlet 206 and a LSPR nanopillar assembly 110. Inlet 202 allows the introduction of fluids, solvents and solutions into the channel 206. The fluids, solvents and solutions travel in the channel 206 and exits via the outlet 204. Nanopillar assembly 110 is positioned such that it is in fluid communication with the channel 206. As a result, nanopillar assembly 110 can interact with the solutions flowing in the channel and thus can be used in sensing the presence of a biomarker when attached to a quantum dot.

In an embodiment, there can be more than one inlet 202. In another embodiment, there can be more than one outlet 204. In another embodiment, for every inlet, there is a corresponding outlet. In another embodiment, there are several outlets for an inlet. In another embodiment, there are several inlets for an outlet. In another embodiment, there are more than one channel connecting the inlet and the outlet. In another embodiment, there are more than one channel and the channels intersect.

Figure 5:
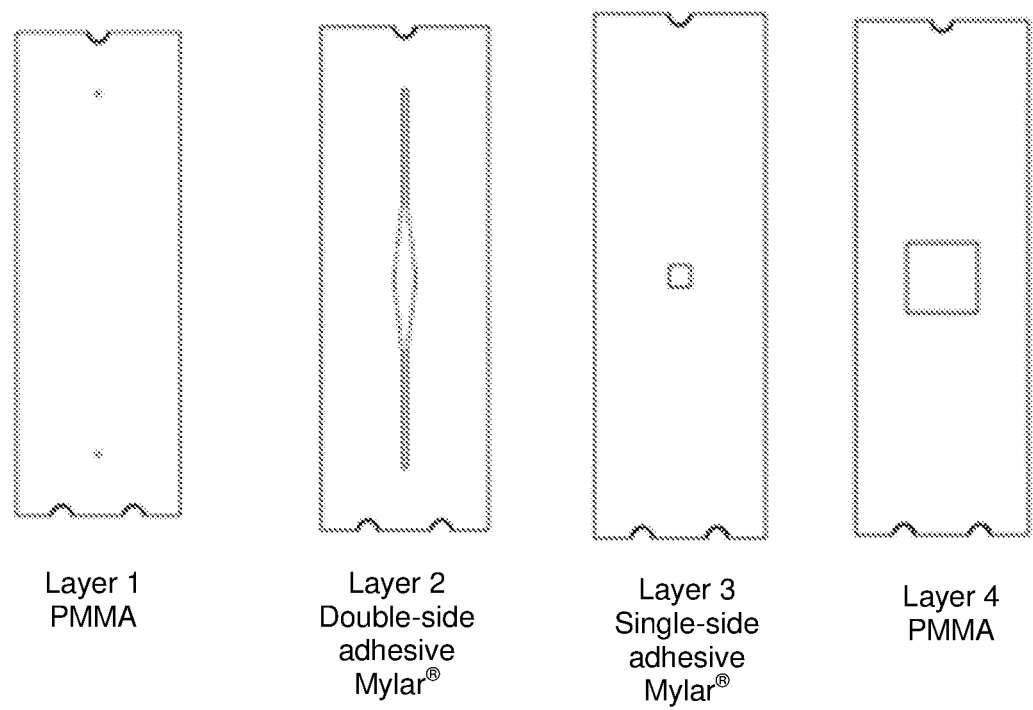
FIG. 5 shows an example of the layers and components of the chip 200.

FIG. 5 shows an example of the layers and components of the chip 200. Each layer is fabricated separately. Layer 1 comprises the inlet 202 and outlet 204. The inlet and outlet act as ports to allow solution flow into and out of the chip. Layer 2 comprises the channel 206. The channel is in fluid communication with the inlet and outlet—i.e. the channel is designed such that the terminal ends of the channel meet the inlet and the outlet when Layers 1 and 2 are combined. This prevents dead volume. Layer 3 comprises a through hole for communicating fluid from the channel onto the nanopillar assembly 110 located in a cavity (or integrally formed onto) Layer 4. The nanopillar assembly 110 is thus positioned such that the whole or part of it is in fluid communication with channel 206 when the layers are combined. Combining these four layers with an adhesive would give at least a workable fluidic chip 200. In some embodiments, Layer 4 may be directly adhered to Layer 2, thereby removing the need for Layer 3.

Layer 4 of fluidic chip 200 can comprise a light transmissible substrate 208. The light transmissible substrate may be positioned at the base of cavity 207. The light transmissible substrate can be any material such as, but not limited to, glass, silicon, poly(methyl methacrylate) (PMMA) or polydimethylsiloxane (PDMS).

The light transmissible substrate 208 is added such that the LSPR nanopillar assembly 110 is disposed between the channel 206 and light transmissible substrate 208. The light transmissible substrate 208 allows the source electromagnetic wave through to the nanopillar assembly 110. Light transmissible substrate 208 serves to protect the LSPR nanopillar assembly from damage or contact. It can also act as a reinforcing layer for the fluidic chip 200.

The light transmissivity of substrate 208 is a measure of the amount of light that can pass through the substrate. The light transmissivity is a physical property of the substrate. The light transmissible substrate may allows 30-100% of the light to be transmitted.

In some embodiments, channel 206 is wider in a vicinity of the LSPR nanopillar assembly 110 than at the inlet 202 and outlet 204. Channel 206 is wider to accommodate the nanopillar assembly 110. The widening of channel 204 also acts to reduce the flow rate of fluids to the nanopillar assembly 110. This increases the residence time or interacting time of the biomarker, quantum dot and antibody with the nanopillar assembly 110. In addition, by maintaining a narrow channel about the inlet and outlet ensure a smaller volume of fluid is necessary to fill the chip 200. This reduces necessary biomarker sample volume.

In another embodiment, channel 204 is wider to accommodate the reduction in the height of channel 204. In another embodiment, channel 204 is wider to increase the spread of the fluids in the region of the nanopillar array. This reduces the potential distance of the biomarker, quantum dot and antibody to the nanopillar assembly 110. As such, attachment can be achieved in a shorter time. In another embodiment, channel 204 is wider to increase the clarity of the fluid filled channel. In another embodiment, channel 204 is wider to increase the transparency of the fluid filled channel. In another embodiment, channel 204 is wider to increase the translucency of the fluid filled channel. In another embodiment, channel 204 is wider to decrease the opaqueness of the fluid filled channel. This is important given that attached quantum dot is in fluid communication with the channel. The transparency of the fluid can influence the sensitivity of the system.

Figure 6:
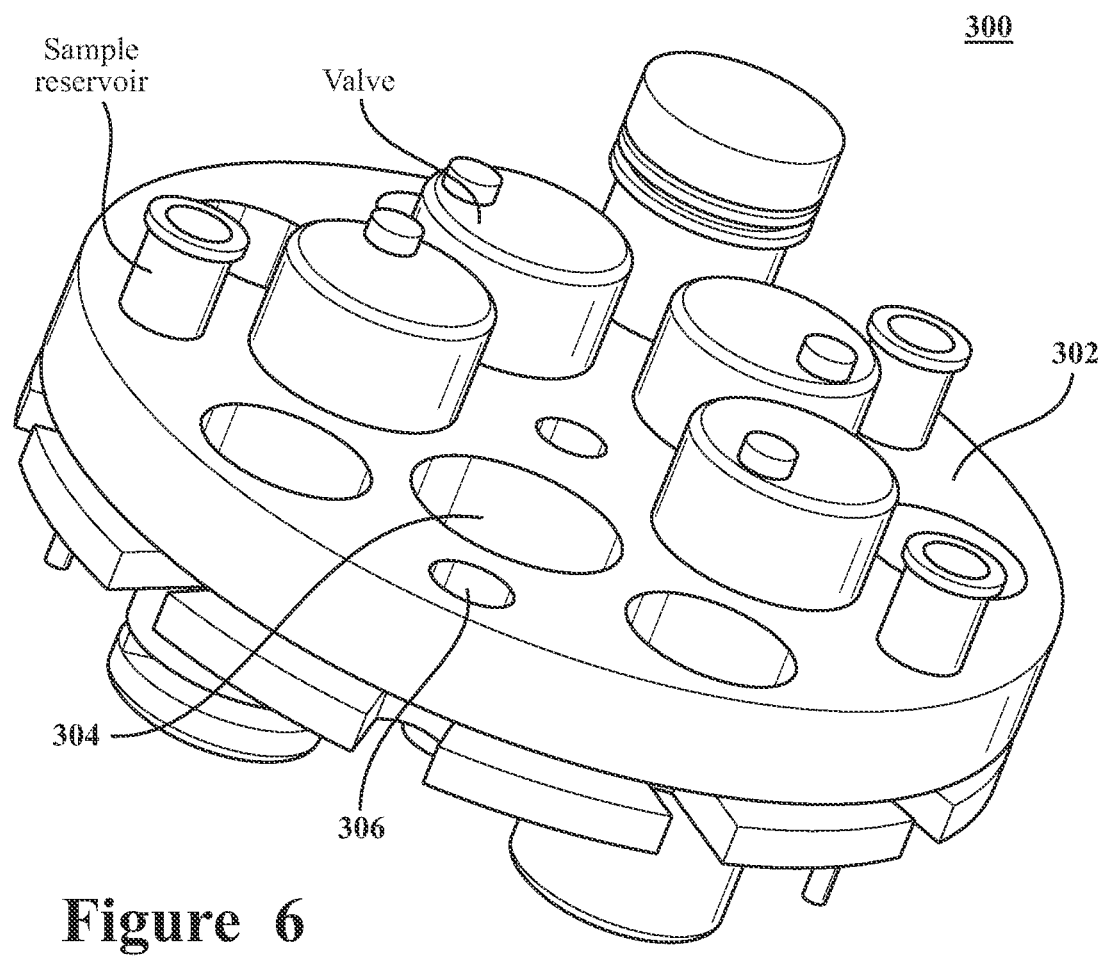
FIG. 6 illustrates an example of a valve assembly 300.

FIG. 6 illustrates an example of a valve assembly 300. Valve assembly 300 comprises a holder 302, at least three valve supports 304 in the holder. For each valve support 304, there is at least one solution reservoir cavity 306. Each solution reservoir cavity 306 is disposed in the holder 302. The valve supports 304 are arranged substantially in a circle about a fixed point of the holder 120. The solution reservoir cavities 306 are positioned substantially circumferentially to the valve supports 304. In some embodiments, the valve supports are arranged in a circular position to minimise tubing connections. In another embodiment, solution reservoir cavities 306 are arranged in a circular position in line with the valves. In another embodiment, the valve support 304, or each valve support 304, contains a valve. The valve can be a non-penetrative valve—i.e. it does not require a member to penetrate any tubing in order to move the valve between the open state in which flow is permitted, and the closed state in which flow is prevented. An example of non-penetrative valve is a pinch valve. In some embodiments, the valve assembly 300 is a non-penetrative valve assembly. For example, valve assembly 300 is a pinch valve assembly.

In use, the cavity 306 contains a sample. The cavity 306 can contain a solution reservoir. The solution reservoir can be a biomarker sample solution, an antibody solution, a quantum dot solution or a flushing solvent.

Figure 7:
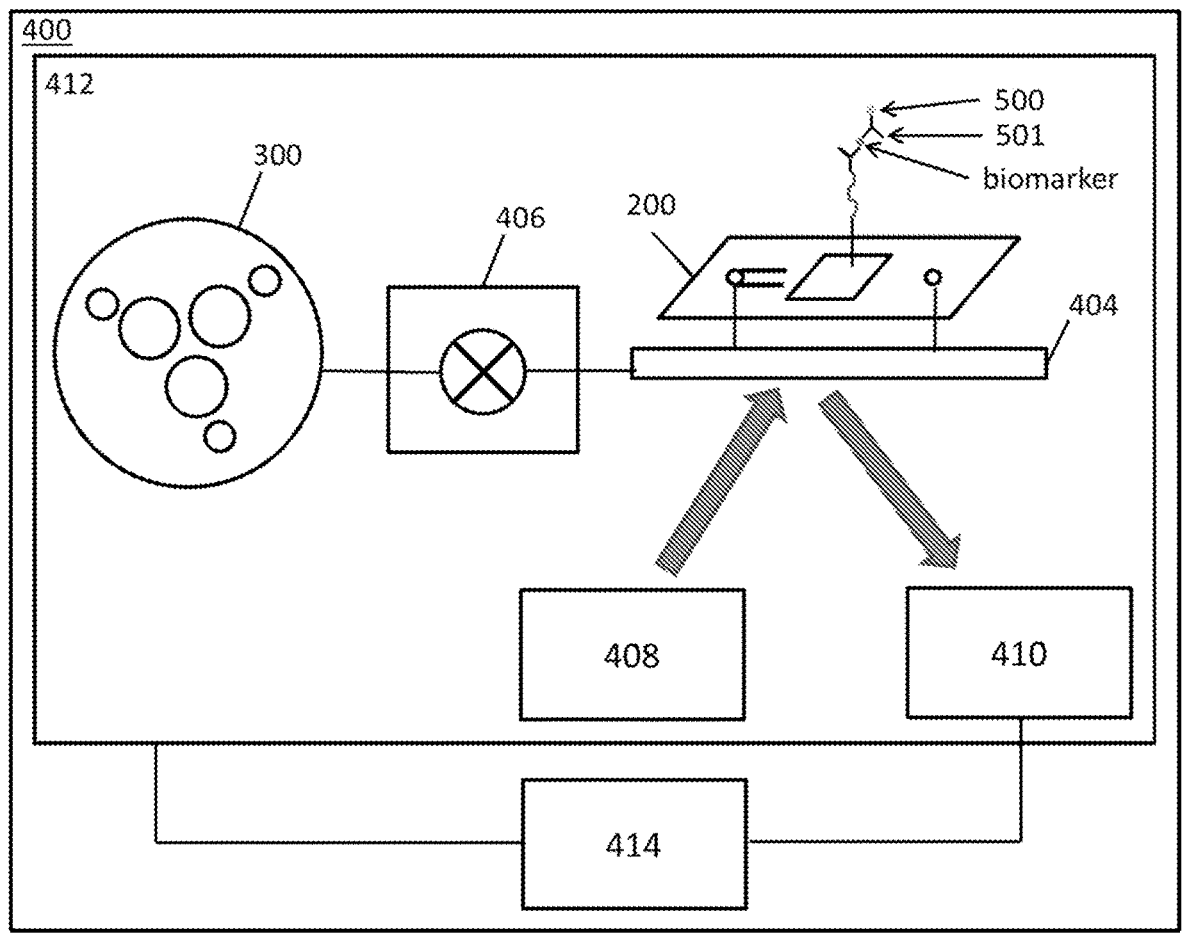
FIG. 7 shows an example of LSPR biomarker detection system 400.

FIG. 7 shows a LSPR biomarker detection system 400. The system 400 is used for sensing a biomarker when attached to a quantum dot 500. The system 400 can be used for sensing procalcitonin (PCT). It does this by detecting an emitted light from the quantum dot 500. This emitted light is a result from the enhancement of the quantum dot excitation energy by the LSPR of the nanopillar assembly 110. With this increase in emitted light, low concentration of biomarker can be detected. Moreover, the frequency of the emitted light can be selected. This enables detected light to be band pass filtered to remove noise.

The system 400 includes solution reservoir 401, 402, 403, a LSPR fluidic chip support 404, flow mechanism 406, valve assembly 300, light source (presently a laser source 408, but may alternatively be a light emitting diode), a detection mechanism 410 and a controller 412. One solution reservoir cavity 306 holds a first solution reservoir containing biomarker sample 401. An example of a biomarker is PCT. The biomarker sample 401 can be either a suspension, solution, or emulsion. The biomarker sample 401 can be whole blood, blood plasma, protein extract, or other bodily fluids, purified, processed or otherwise. The biomarker sample 401 can also be spiked standards or other non-biological fluids that can be used to calibrate the system 400. Another solution reservoir cavity 306 holds a second solution reservoir containing a further biomarker antibody solution 402. The reason the term "further biomarker antibody" is used, is that the first biomarker antibody, attached to the spacer and thereby to the nanopillar array, will often be supplied with the chip. Thus the "further biomarker antibody" is one applied after the biomarker sample has been flowed through the chip, to facilitate attachment of the quantum dot. The first biomarker antibody and further biomarker antibody may be the same, or may be different depending on the biomarker being detected, the affinity to the biomarker, and the functionalisation of the quantum dot.

The further biomarker antibody solution 402 contains the further biomarker antibody 501. The further biomarker antibody solution 402 can be a suspension, solution, or emulsion. The antibody 501 has an affinity for the biomarker in the biomarker sample 401. For example, the further biomarker antibody 501 is PCT antibody if the biomarker in the biomarker sample 401 is PCT. The further biomarker antibody 501 can be further modified or functionalised. For example, the further biomarker antibody 501 can be modified with a biotin, so as to receive a streptavidin modified quantum dot 500. In another embodiment, the further biomarker antibody 501 is modified using click chemistry, to allow a complementarily modified quantum dot 500 to attach. A third solution reservoir cavity 306 holds a quantum dot solution 403 containing quantum dot 500. The quantum dot 500 is selected so that its excitation wavelength overlaps with the LSPR resonance wavelength. The quantum dot 500 is also selected so that its emission wavelength does not overlap with the LSPR resonance wavelength. This ensures the LSPR resonance can be filtered from the detected emission from the quantum dots and thus does not interfere with that emission. For example, 655 nm emission quantum dots can be used. The quantum dot 500 can be modified to attach to the further biomarker antibody 501. The modification of the quantum dot 500 is complementary to the modification on the further biomarker antibody 501.

In some embodiments, biological interaction is used to attach the quantum dot 500 to the further biomarker antibody 501. In other embodiments, biotin-streptavidin interaction is used. In other embodiments, biotin-avidin interaction is used. In another embodiment, click chemistry is used. In another embodiment, thiol-ene reaction is used. In another embodiment, thiol-yne reaction is used. In another embodiment, urea type reaction is used. In another embodiment, isonitrile-tetrazine reaction is used. In another embodiment, Diels-Alder reaction is used. In another embodiment, [3+2] cycloaddition reaction is used. In another embodiment, [4+1] cycloaddition reaction is used.

Figure 8:
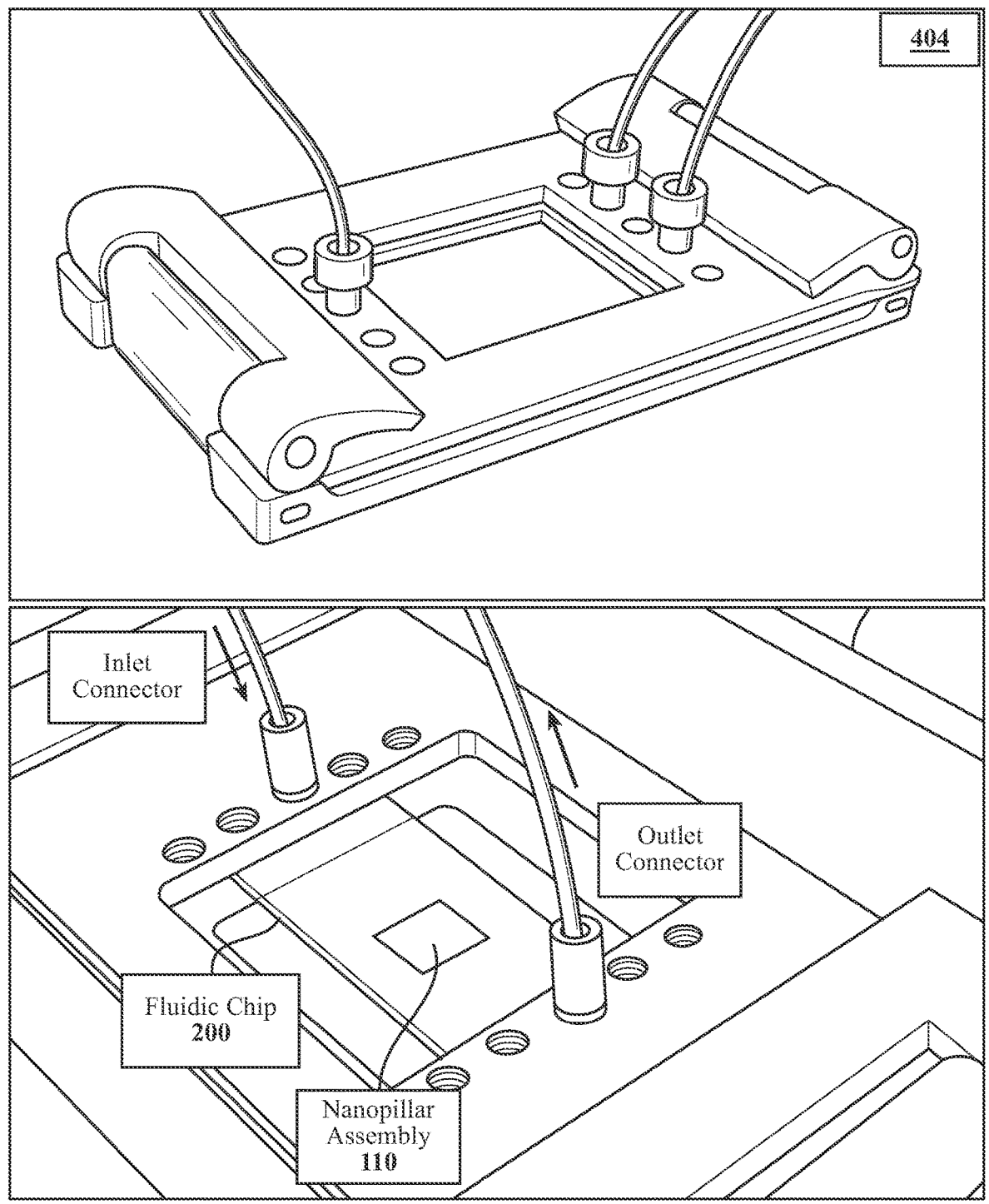
FIG. 8 shows an example of LSPR fluidic chip support 404.

FIG. 8 shows an example of LSPR fluidic chip support 404 adapted to receive a LSPR fluidic chip 200. Support 404 can be Chipholder AHQ 010 from SIMTech. Support 404 fixes chip 200 firmly in place. Support 404 can further comprise a locking mechanism to fix the chip 200 in place. Support 404 comprises an inlet connector for connecting to an inlet of chip 202. Support 404 also comprises an outlet connector for connecting to an outlet of chip 204. In this way, support 404 allows for fluid communication between the valve assembly 300 and chip 200, and reduces the potential of leakage. The support 404 can further comprise a locking mechanism at the inlet connector and at the outlet connector. In another embodiment, support 404 provides leak-proof fluid communication between the valve assembly 300 and the chip 200. In another embodiment, support 404 comprises a slit to allow electromagnetic wave through to the chip 200. In another embodiment, support 404 comprises an orifice to allow electromagnetic wave through to the chip 200.

The flow mechanism 406 comprises a pump system. The pump system is in fluid communication with the inlet connector of chip 200. Flow mechanism 406 (e.g. using the pump system) dispenses content from the first solution reservoir 401, second solution reservoir 402 and third solution reservoir 403 into the LSPR fluidic chip 200 via the inlet connector. In an embodiment, flow mechanism 406 comprises a pump. The pump displaces fluid from each reservoir. Alternatively, a separate pump may be provided for each reservoir.

The pump can be a positive displacement pump. An example is a peristaltic pump. Liquid is contained within a flexible tube fitted inside a circular pump casing. The flexible tube is not pierced. A rotor with rollers compresses the flexible tube. As the rotor turns, the part of the tube under compression is pinched closed thus forcing the liquid to be pumped to move through the tube. In this way, liquid is transported, at ambient pressure, toward the pump outlet. The amount of liquid flowing can be controlled by setting the voltages and the size of the tubing. Increasing the voltages will increase the flow rate. Smaller tube diameter size can allow more flow of liquid. In some embodiments, the range of the flow rate is set from 0-1.1V (0-1.1 ml/min). The flow rate may be 0.1, 0.2, 0.3, 0.4, 0.5, 0.6, 0.7, 0.8, 0.9, 1.0, 1.1 mL/min, or any values within the range.

In an embodiment, the valve assembly 300 is a pinch valve assembly. Pinch valve controls flow passage through a flexible tube. When the tubing is pinched, a tight seal results which prevents fluid from passing through. When the tubing is not pinched, fluid is allowed to flow through. In another embodiment, valve assembly 300 comprises an open state and a closed state for the first solution reservoir 401. In another embodiment, valve assembly 300 comprises an open state and a closed state for the second solution reservoir 402. In another embodiment, valve assembly 300 comprises an open state and a closed state for the third solution reservoir 403. When in the open state, reservoirs 401, 402 and 403 are in fluid communication with the LSPR fluidic chip support 404. When in the closed state, reservoirs 401, 402 and 403 are not in fluid communication with the LSPR fluidic chip support 404.

In some embodiments, the valve assembly 300 further comprises an 8-into-1 manifold. In other embodiments, the 8-into-1 manifold provides fluid communication of reservoirs 401, 402 and 403 with the support 404. The 8-into-1 manifold allows a reservoir to flow its solution to the support 404, when the valve places that reservoir in fluid communication with the support 404.

For example, when reservoir 401 is in fluid communication with the support 404, reservoirs 402 and 403 are not in fluid communication with the support 404.

The laser source 408 directs a source electromagnetic wave through the LSPR fluidic chip 200. In the present embodiment, the size of the laser head dimension is less than 150×60×50(H) mm. The laser controller dimension is less than 170×150×90(H) mm. The source electromagnetic wave generates the LSPR on the nanopillar assembly 110. The LSPR then interacts with the quantum dot.

In an embodiment, the laser source 408 is a solid-state laser source. In other embodiments, the laser source may be:
- a gas laser source;
- a chemical laser source;
- a dye laser source;
- a metal-vapour laser source;
- a semiconductor laser source;
- a continuous wave laser source;
- a 532 nm wavelength laser, a 633 nm wavelength laser, a 473 nm wavelength laser or a 405 nm wavelength laser.

The laser source 408 may have any appropriate output (e.g. 100 mW). In some cases, the output is tunable from 0-100%.

Detection mechanism 410 comprises a photodetector for detecting an emitted electromagnetic wave originating from the quantum dot 500. The photodetector can be a camera. In another embodiment, the photodetector is a VS14 1.4M Pixel CCD camera. The VS14 camera has dimensions of less than 1.50×150×70 mm. In another embodiment, the photodetector allows for a long exposure. In another embodiment, the photodetector allows for a low light detection. The camera is used for fluorescence measurement to detect the presence of quantum dot binding onto the PCT.

Controller 412 can be used to operate the flow mechanism 406, valve assembly 300, laser source 408 and detection mechanism 410 by any known mechanism, such as by varying a supply voltage between 0V and more than 0V. Controller 412 can sequentially dispense the biomarker sample 401, biomarker antibody solution 402 and quantum dot solution 403 through the inlet connector, activate and deactivate the laser source 408 and detection mechanism 410. The system, for example in the controller, comprises a data acquisition unit for storing the data generated by the detector.

The controller operates the valve assembly by regulating the timing of movements of respective valves between open and closed states—e.g. using a digital output signal for each valve. For this purpose, the controller 412 may be connected to an external 12V power supply. The controller may thus supply power to the valves to actuate the valves. The controller 412 comprises a printed circuit board (PCB) for governing transmission of signals to respective valves, flow mechanism and so forth.

Using the power source, the controller 412 can control the timing to on or off the valves, the flow rate of the pump system, the timing and operation of the light source and detection mechanism (i.e. the photodetector or camera).

Figure 9:
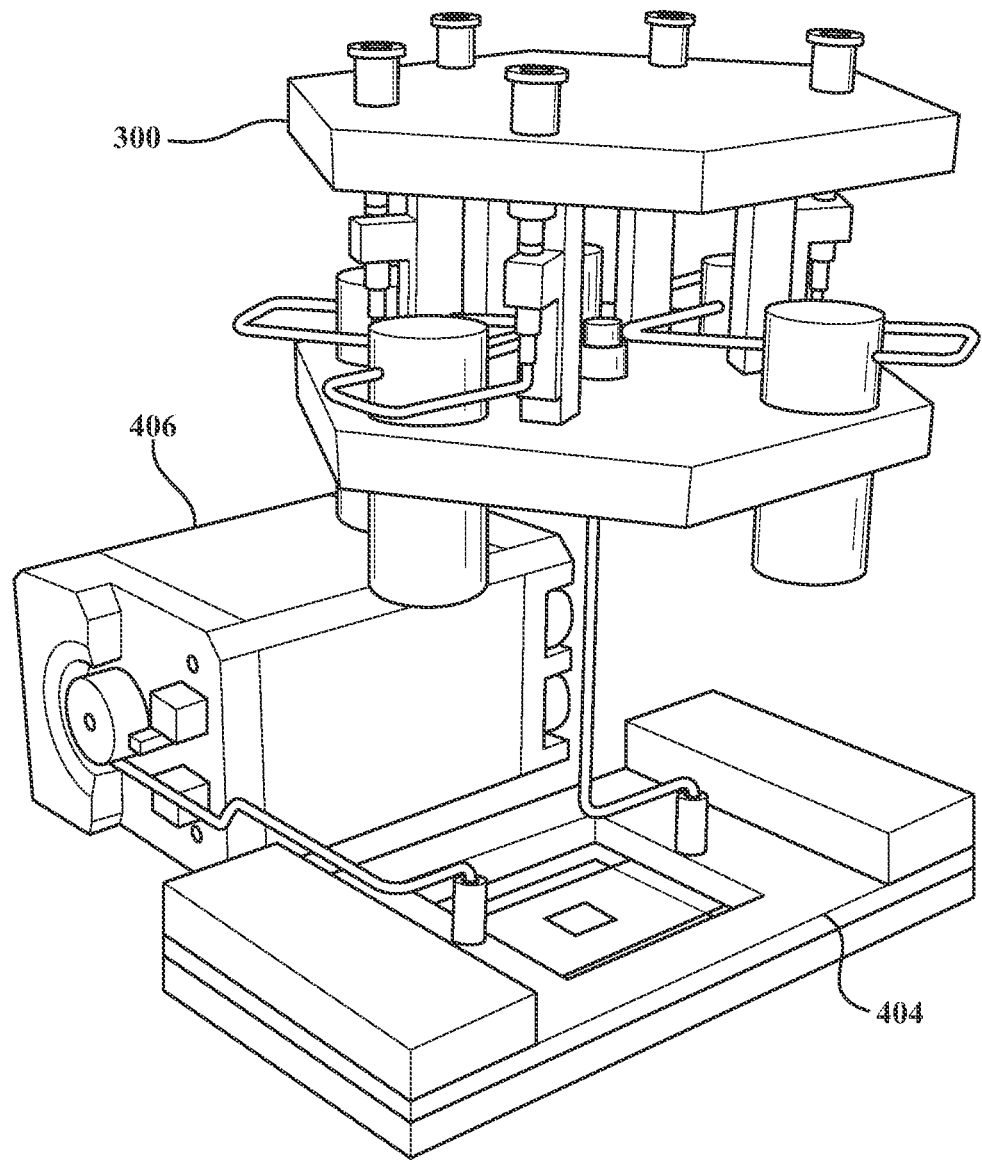
FIG. 9 shows an example of such a possible arrangement of the chip support 404, valve assembly 300 and flow mechanism 406.

In an embodiment, the system 400 comprises LSPR fluidic chip support 404 positioned substantially adjacent the valve assembly 300. In another embodiment, valve assembly 300 is disposed between the flow mechanism 406 and the LSPR fluidic chip support 404. FIG. 9 shows an example of such a possible arrangement. In this example, peristaltic pump and pinch valves are used to control the movement of liquid samples from the valve assembly 300 to a chip support 404. A liquid sample is introduced to tube channel by opening the selected valve at a specific timing. The pump is activated to move the liquid sample via a 8-into-1 manifold to the support 404. The liquid sample moves along the tubing by the action of the pump. The flow rate can be controlled by varying voltages. The flow rate can also be varied by changing the size of the tubing attached to the flow mechanism 406. The flow mechanism 406 can be positioned below the valve assembly 300 to prevent any backflow of the liquid.

Detection mechanism 410 can further comprises focusing lens. The focusing lens is used to focus the source electromagnetic wave onto the nanopillar assembly 110 and quantum dot 500. Focusing lens is also used to focus the emitted electromagnetic wave onto the photodetector.

Detection mechanism 410 can further comprises a beam splitter. The beam splitter is an optical device which can split an incident light beam into two or more beams, which may or may not have the same optical power. In an embodiment, the beam splitter reflects wavelengths below about, say, 565 nm and permits wavelengths of about 600 nm to 700 nm.

Detection mechanism 410 can further comprises a bandpass filter. The bandpass filter is a device that passes frequencies within a certain range and rejects frequencies outside that range. In an embodiment, the bandpass filter allows about 655, or about 655±15 nm light to pass through.

Figure 10:
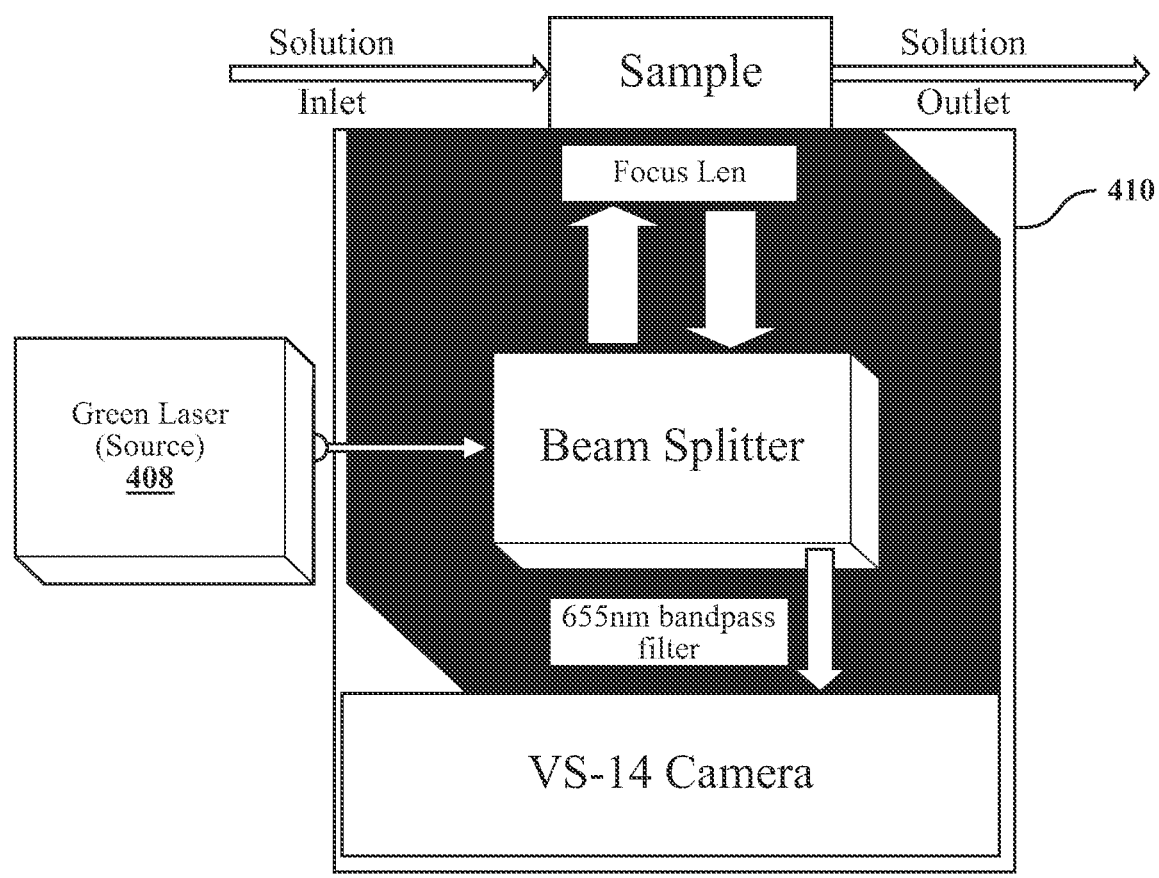
FIG. 10 shows a possible schematic arrangement of the detection mechanism 410.

FIG. 10 shows a possible arrangement of the detection mechanism. The detector mechanism 410 is completely enclosed in a black box using light absorption material with no reflection. As such, zero percent light enters the box. This ensures that the light detected is solely from quantum dot emission. The laser source 408 (for example 532 nm laser) connects to the detection mechanism 410 via the optical fiber cable. The light passes through the beam-splitter and transmits onto the chip support 404, which can hold the chip 200. In the presence of quantum dot 500 (for example 655 nm emitting quantum dot), 655 nm wavelength will be emitted. The emitted light will pass through the bandpass filter (for example 655 nm bandpass filter) and onto the photodetector (for example camera) for detection.

Figure 11:
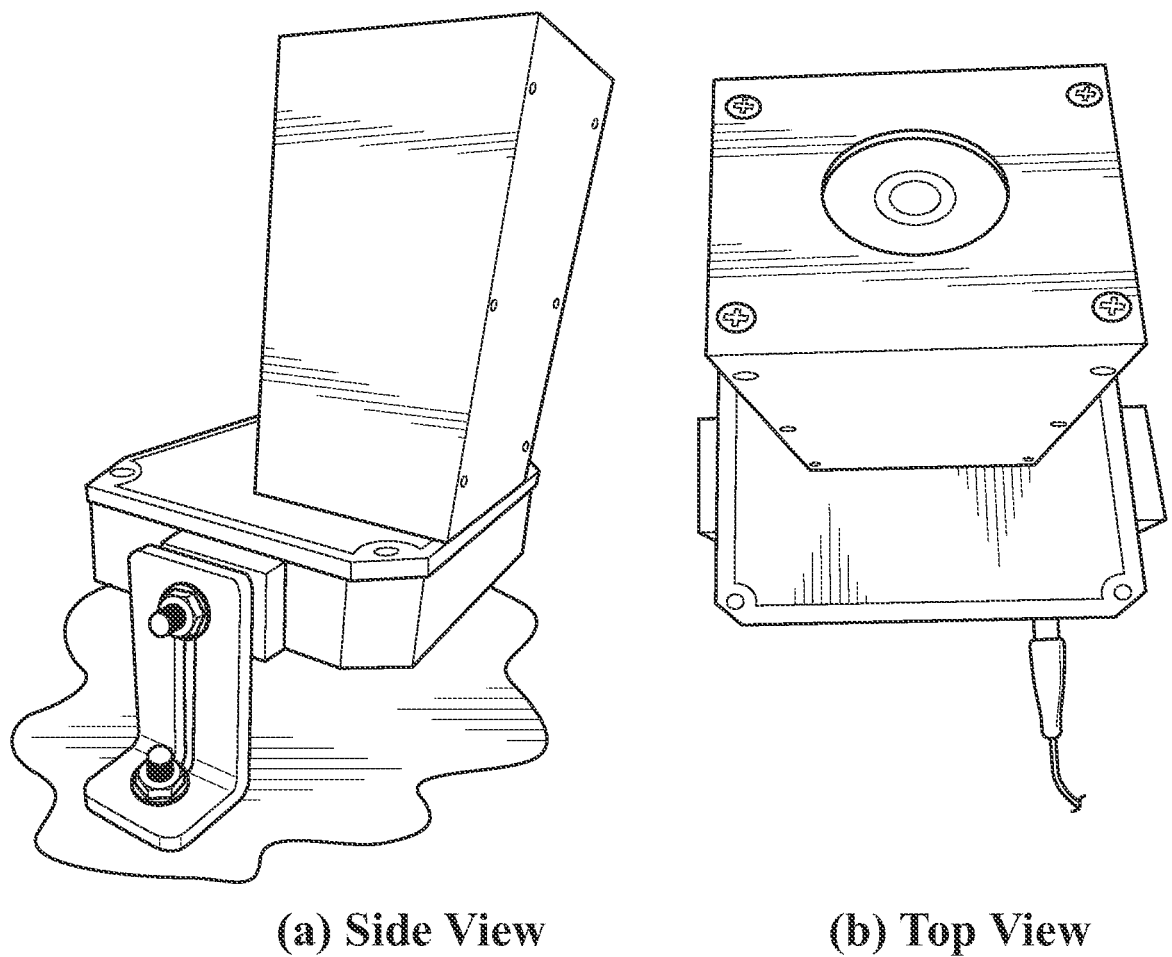
FIG. 11 illustrates an example of a possible arrangement of the detection mechanism 410.

FIG. 11 illustrates an example of the physical arrangement of the detection mechanism. In an embodiment, the detection mechanism 410 is arranged to only detect an intensity of the emitted electromagnetic wave originating from the quantum dot 500.

Figure 12:
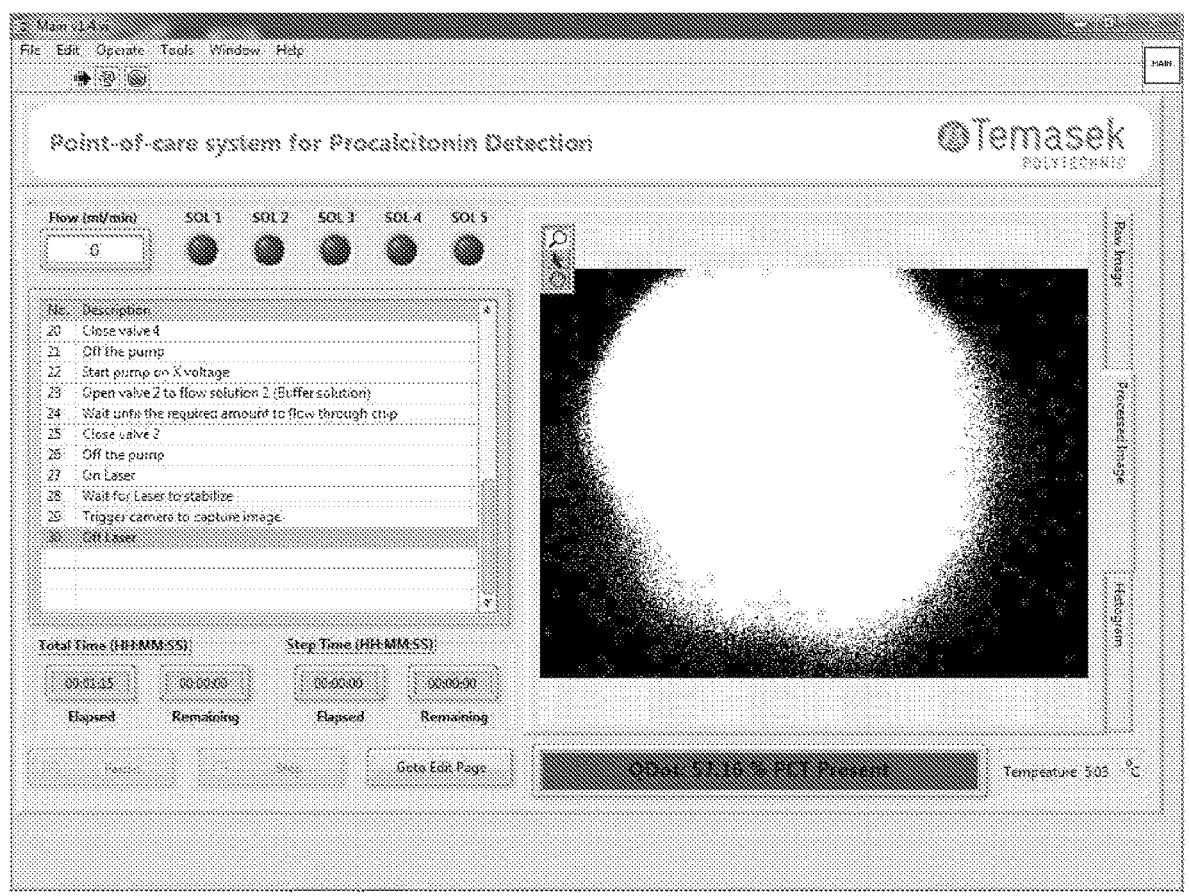
FIG. 12 shows an example of a screenshot of the screen 414.

The biomarker detection system 400 can further comprise a screen 414. In particular, the screen can be positioned to face a user when in use. The screen can be a touch screen. In particular, the screen can be a 5-wire resistive touch screen. FIG. 12 shows an example of a screenshot of the screen. In the embodiment shown, the screen 414 displays:
- an intensity of the emitted electromagnetic wave originating from the quantum dot 500;
- the percentage correlating to full saturation of quantum dot 500—the output required to exhibit "full saturation" can be calibrated depending on the biomarker being sensed, the concentration of the biomarker in the sample, the equipment from which the system is built and so on;
- the concentration of the biomarker detected from the biomarker sample;
- the sequences of the method herein described (shown in numbered steps on the left-hand side of the screen);
- the current step of the method being executed;
- the time elapsed of the sequence step;
- the time remaining of the sequence step;
- the total time elapsed;
- the total time remaining;
- the captured image of the nanopillar assembly 110;
- the flow rate; and
- results from previous biomarker samples.

The biomarker detection system 400 can further comprise a fourth sample reservoir containing a solvent 416. The flow mechanism 406 is adapted to dispense contents of the solvent 416 into the LSPR fluidic chip support 404 and chip 200 via the inlet connector. The valve assembly 300 further comprises an open state in which the fourth reservoir is in fluid communication with the LSPR fluidic chip support 404. The valve assembly 300 further comprises a close state in which solvent 416 is not in fluid communication with the LSPR fluidic chip support 404.

In some embodiments, the solvent 416 is an aqueous medium. The term 'aqueous medium' used herein refers to a water based solvent or solvent system, and which comprises of mainly water. Such solvents can be either polar or non-polar, and/or either protic or aprotic. Solvent systems refer to combinations of solvents which resulting in a final single phase. Both 'solvents' and 'solvent systems' can include, and is not limited to, pentane, cyclopentane, hexane, cyclohexane, benzene, toluene, dioxane, chloroform, diethylether, dichloromethane, tetrahydrofuran, ethyl acetate, acetone, dimethylformamide, acetonitrile, dimethyl sulfoxide, nitromethane, propylene carbonate, formic acid, butanol, isopropanol, propanol, ethanol, methanol, acetic acid, ethylene glycol, diethylene glycol or water. Water based solvent or solvent systems can also include dissolved ions, salts and molecules such as amino acids, proteins, sugars and phospholipids. Such salts may be, but not limited to, sodium chloride, potassium chloride, ammonium acetate, magnesium acetate, magnesium chloride, magnesium sulfate, potassium acetate, potassium chloride, sodium acetate, sodium citrate, zinc chloride, HEPES sodium, calcium chloride, ferric nitrate, sodium bicarbonate, potassium phosphate and sodium phosphate. As such, biological fluids, physiological solutions and culture medium also falls within this definition.

In an embodiment, the sequences are first selected and added to the controller 412. The controller 412 is adapted to perform the following steps:
1) the controller run the sequences assigned;
2) the screen displays the full sequence list;
3) the screen displays the current sequence and the remaining time;
4) the light source is switched on;
5) image is captured by the camera with exposure time of 4 seconds;
6) the captured image is processed and analyzed;
7) the percentage is displayed which correlates to the concentration of quantum dot; and
8) the screen shows the PCT concentration based on the intensity of the quantum dot emission.

The controller 412 is adapted to perform the following steps:
a) start flow of biomarker sample into the LSPR fluidic chip by operating the valve assembly so that the first solution reservoir is in communication with the LSPR fluidic chip support;
b) dispense biomarker sample into the LSPR fluidic chip by operating the pump system;
c) stop flow to the LSPR fluidic chip by operating the valve assembly so that the first solution reservoir is not in fluid communication with the LSPR fluidic chip support;
d) start flow of further biomarker antibody to the LSPR fluidic chip by operating the valve assembly so that the second solution reservoir is in communication with the LSPR fluidic chip support;
e) dispense further biomarker antibody into the LSPR fluidic chip by operating the pump system;
f) stop flow to the LSPR fluidic chip by operating the valve assembly so that the second solution reservoir is not in fluid communication with the LSPR fluidic chip support;

g) start flow of quantum dot to the LSPR fluidic chip by operating the valve assembly so that the third solution reservoir is in communication with the LSPR fluidic chip support;

h) dispense quantum dot into the LSPR fluidic chip by operating the pump system;

i) stop flow to the LSPR fluidic chip by operating the valve assembly so that the third solution reservoir is not in fluid communication with the LSPR fluidic chip support;

j) direct the source electromagnetic wave through the LSPR fluidic chip; and k) detect the intensity of the emitted electromagnetic wave originating from the quantum dot.

The controller 412 may further be adapted to repeat the steps of:

l) flushing the LSPR fluidic chip by operating the valve assembly so that the fourth solution reservoir is in communication with the LSPR fluidic chip support;

m) dispensing solvent into the LSPR fluidic chip by operating the pump system;

n) stopping flushing the LSPR fluidic chip by operating the valve assembly so that the fourth solution reservoir is not in fluid communication with the LSPR fluidic chip support, between steps c) and d), f) and g), and i) and j).

Figure 13:
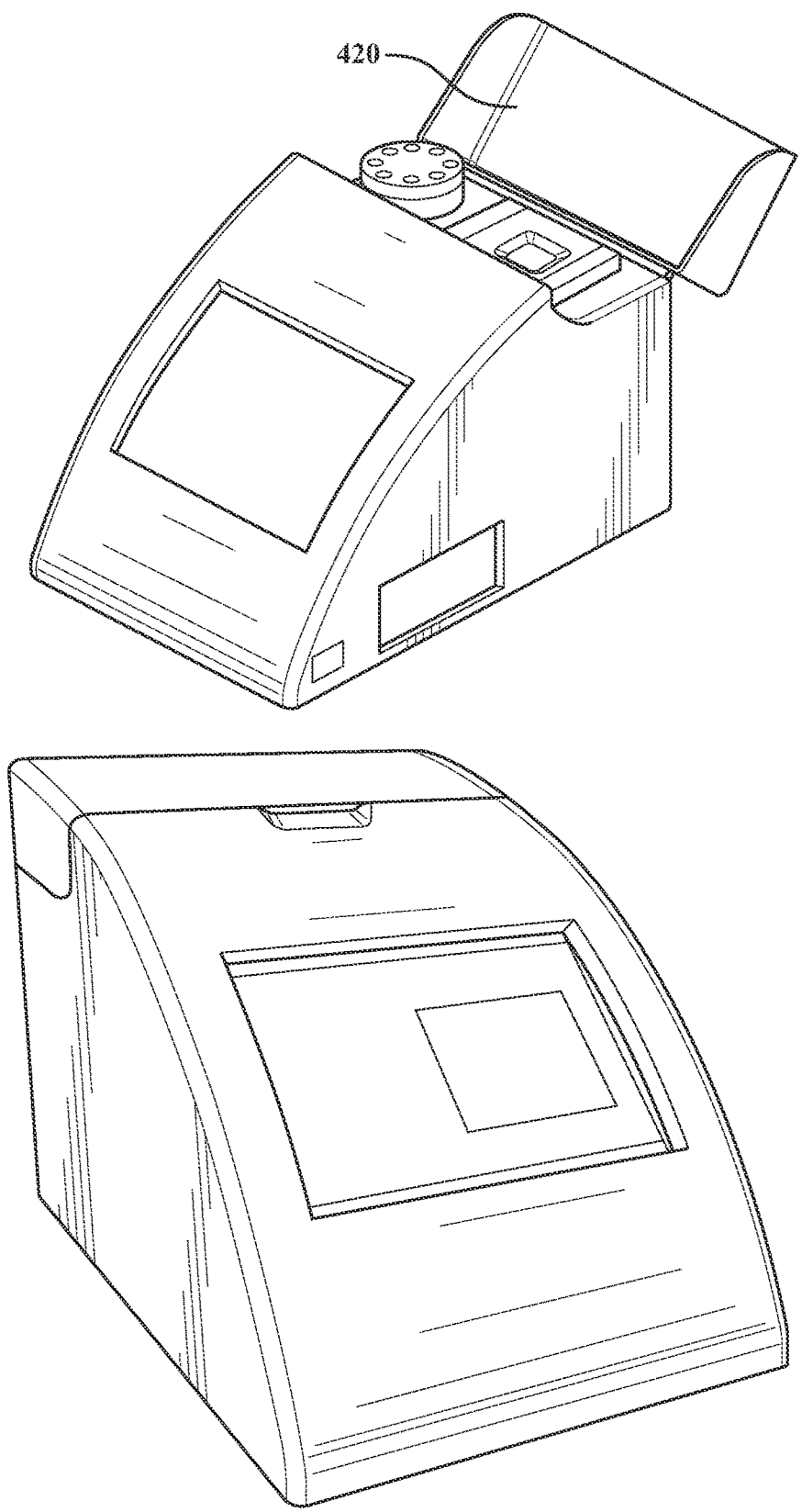
FIG. 13 shows an example of system 400.

FIG. 13 shows an example of system 400. All the components as shown in FIG. 7 are held within the casing. The casing of system 400 can be printed by 3D printer using ABS materials.

All parts are assembled using superglue to form the casing. The valve assembly 300 and chip support 404 are accessible via a flap 420 at the top, presently shown in the open position. This allows samples to be added to the sample reservoir cavity 306 and the chip 200 to be fixed onto the support 404 with ease. The flap is then lowered to cover the support 404. This prevents ambient light from interfering with the detection. Part of the casing is exposed to reveal the screen. This allows a user easy access to the controller and to run the system.

A method for detecting a biomarker in a sample is also disclosed. The method comprises:

a) selecting a polymer spacer;

b) attaching the polymer spacer to a nanopillar;

c) attaching a biomarker antibody to the polymer spacer, the polymer spacer being selected so as to have a specific number of monomer units so that a combined height of the polymer spacer and biomarker antibody, when in use with a biomarker and a quantum dot, positions the quantum dot at a predetermined distance from the nanopillar;

d) contacting the biomarker to the biomarker antibody;

e) contacting a further biomarker antibody to the biomarker;

f) attaching the quantum dot to the further biomarker antibody;

g) directing a source electromagnetic wave through the nanopillar; and h) detecting an intensity of an emitted electromagnetic wave originating from the quantum dot.

In another embodiment, the method can detect a biomarker concentration of at least about 0.5 ng/mL can be detected with at least about 50 µL of sample in at least about 30 minutes. In another embodiment, the method can detect PCT. In another embodiment, the method is a PCT detection method.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Certain embodiments of the invention will now be described with reference to the following examples which are intended for the purpose of illustration only and are not intended to limit the scope of the generality hereinbefore described.

Example

LSPR Nanopillar Assembly Fabrication

The gold nanopillar array sensor chip (LSPR nanopillar assembly 110) was fabricated by mass fabrication via nano-imprinting on 4" wafer. The designed gold nanopatterns is first written by e-beam lithography on a silicon wafer. After photoresist development, a seed metal layer is coated on the gold surface. A nickel layer which can be up to 300 µm thick is then electroplated on the silicon wafer. After separation, a 4" nickel mold is obtained. This nickel mold is used to nanoimprint on a 4" glass wafer coated with UV curable photoresist. After nanoimprinting, gold film is deposited on the nanoimprinted photoresist. Gold nanostructures were obtained after photoresist lift-off. Finally, the glass wafer is diced into LSPR nanopillar (110).

Each LSPR nanopillar array sensor chip (LSPR nanopillar assembly 110), is 1 cm×1 cm with the central 0.9 mm×0.9 mm area covered by gold nanopillars and the remaining areas were bare glass. The resultant gold nanopillar array has a pitch of 320 nm, size of 140 nm×140 nm and height of 55 nm (the metal layer includes 5 nm of chromium as the adhesive layer and 50 nm of gold for plasmonic generation). The SEM image of the gold nanopillar array is shown in FIG. 1.

Figure 14:
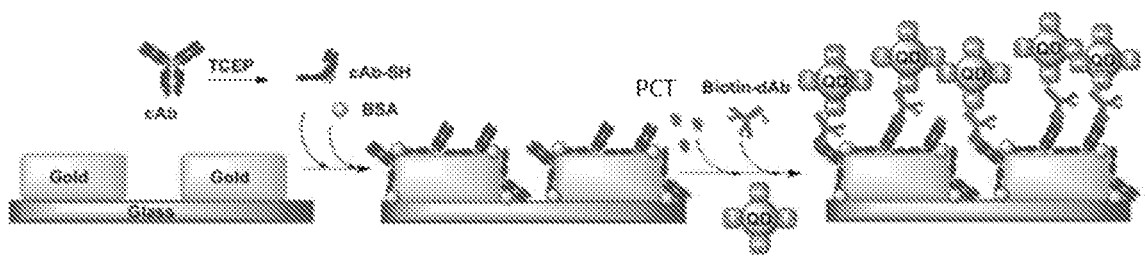
FIG. 14 illustrates a surface modification method (comparator) and its subsequent biomarker detection using quantum dot.

Surface Modification (Comparator):

tris(2-carboxyethyl)phosphine (TCEP) solution was prepared at 50 mM (2.5 mg dissolved in 174 µL of water), and diluted to 250 µM. 5 µL of the diluted TCEP solution was added to 50 µL of the PCT antibody in phosphate buffered saline (PBS) (1.26 mg/ml, 8.4 µM) and incubated at room temperature for 30 minutes. After reaction, the mixture was purified by G25 column. The purified cleft anti-PCT (cAb-SH) was stored at 4° C. and diluted with 4-(2-hydroxyethyl)-1-piperazineethanesulfonic acid (HEPES) buffer before use. A nanopillar sensor chip (LSPR nanopillar assembly 110) was treated in a UV/O3 chamber for 7 min. The freshly cleaned array was rinsed with water and then immersed in the diluted cAb-SH solution (50 µg/ml in HEPES) at 4° C. overnight. After the nanopillar sensor chip (LSPR nanopillar assembly 110) was cleaned by HEPES, bovine serum albumin (BSA) solution (3 mg/ml) was applied onto the surface for 10 minutes to block the cAb-SH uncovered area. The chip was rinsed 3 times with HEPES buffer to remove the unbound proteins. FIG. 14 illustrates this surface modification method and the subsequent PCT detection using quantum dot.

Figure 15:
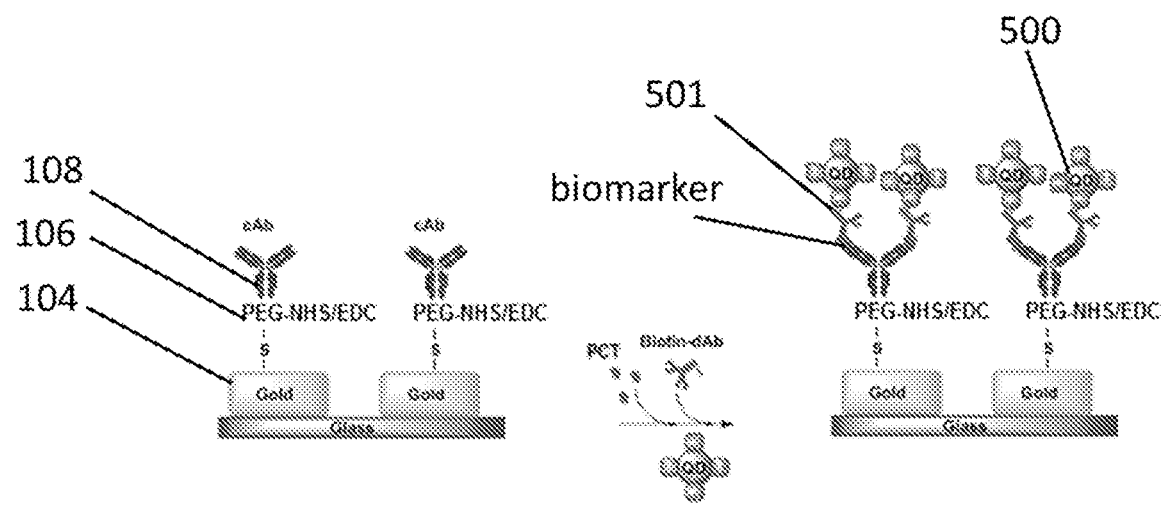
FIG. 15 illustrates a surface modification method (present invention) and its subsequent biomarker detection using quantum dot.

Surface Modification with Polymer Spacer:

A nanopillar sensor chip (LSPR nanopillar assembly 110) was cleaned in the order of isopropanol, acetone and deionized water and dried at room temperature with nitrogen gas prior to chemical modifications. An amine-reactive self-assembly monolayer (SAM) was formed by incubating the sensor chips in ethanolic solution of 1 mM $PEG_7$ thiol acid (thiol-COOH, Poly-pure AS, Norway) overnight at room temperature, then washed thoroughly with pure ethanol and dried in room temperature. Subsequently, the sensor was incubated in a mixture of 75 mM of sulfo-N-hydroxysuccinimide (sulfo-NHS) and 15 mM of 1-ethyl-3-(3-dimethylaminopropyl) carbodiimide (EDC) (Bio-Rad, Hercules, Calif., USA), to activate the carboxylic group of the SAM for 15 min. Next, 30 μl of 50 μg/ml anti-PCT (Anti-Procalcitonin mouse monoclonal antibody, Abcam) was spotted on the sensor surface and incubated for 2 hours. Finally, the sensor chip (LSPR nanopillar assembly 110) was immersed in 1 M of ethanolamine-HCl solution (Bio-Rad, Hercules, Calif., USA) for 15 min to deactivate the unreacted carboxylic acid groups, followed by a rinse with deionized water and dried with nitrogen gas. FIG. 15 illustrates this surface modification method and the subsequent PCT detection using quantum dot.

LSPR Fluidic Chip

Microfluidic chip was designed and fabricated to integrate with nanopillar array sensor chip (LSPR nanopillar assembly 110) for liquid bio-reagents and buffer solutions delivery and processing. Low cost PMMA and adhesive Mylar® were chosen for the fabrication. Four-layer structures, as shown in FIG. 5, were designed and fabricated with inlet/outlet on Layer 1(PMMA), fluidic channel on layer 2 (double-side adhesive Mylar®), a though hole to expose the nanopillar array structure to the fluidic channel on layer 3 (single-side Mylar®) and a nanopillar assembly 110 on layer 4 (PMMA). All the structures were cut through using a $CO_2$ laser cutter. The four layers were laminated together to form the final microfluidic chip with nanopillar array sensor chip stick to the layer 3 adhesive Mylar® and face to the fluidic channel. FIG. 4 shows the fabricated microfluidic chip (fluidic chip 200) with gold nanopillar array chip (LSPR nanopillar assembly 110) integrated.

PCT Detection Using Biomarker Detection System

The microfluidic chip (fluidic chip 200) integrated nanopillar array sensor chip (LSPR nanopillar assembly 110) was placed on the microfluidic chipholder (chip support 404) and connected to the microfluidic delivery system (system 400). 100 μl of 1% BSA solution was supplied and flowed through the nanopillar array surface (LSPR nanopillar assembly 110) and incubated for 10 min to block any non-specific binding. After 2 min phosphate-buffered saline with Tween-20 (PBST) flush, 50 μl PCT solution with various concentration (Active human procalcitonin full length protein, Abcam) was applied and incubated for 10 min to react with capture antibodies which were immobilized on the nanopillar array. PBST was flowed for 2 min to remove unreacted PCT before 50 μl biotin-dAb (20 μg/ml, Biotin Conjugated Mouse Anti-Procalcitonin, Raybiotech) flowed in and incubated for 10 min. After that, the chip (fluidic chip 200) was flushed with PBST again for 2 min, followed by applying 50 μl of streptavidin conjugated QD-655 (20 nM, Life Technology) and incubating for 10 min. The unbound QD-655 was flushed away by PBST for washing 2 min. The sandwich cAb/PCT/biotin-dAb/QD-655 immuno-structure was built on the nanopillar chip (LSPR nanopillar assembly 110).

Biomarker Detection System Performance

Figure 16:
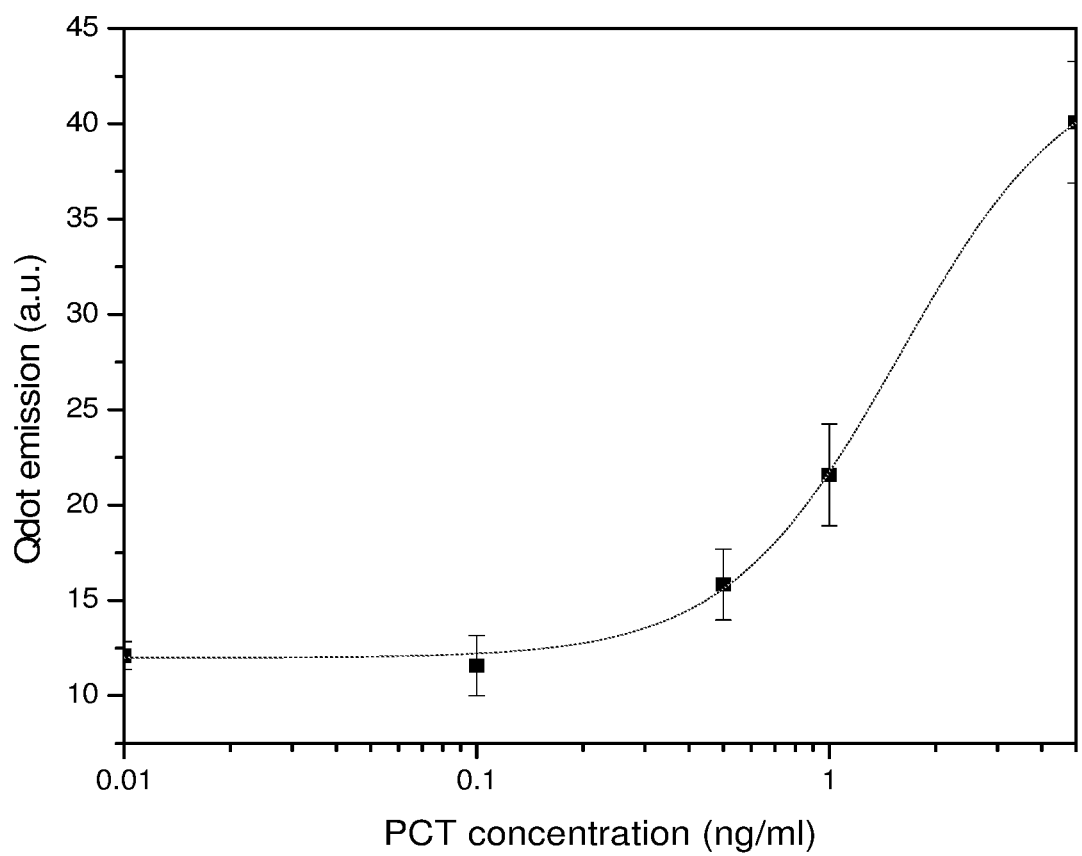
FIG. 16 illustrates the relationship of PCT concentration (ng/mL) against quantum dot emission (A.U.).

PCT solutions with various concentrations (10 ng/ml, 5 ng/ml, 1 ng/ml, 0.5 ng/ml, 0.1 ng/ml) flowed in the microfluidic channel. After the sandwich cAb/PCT/biotin-dAb/QD-655 immuno-structure was built, the nanopillar array sensor chip (LSPR nanopillar assembly 110) were exposed to laser beam excitation for QD fluorescent measurement by opening the shutter which is located between the microfluidic chip (fluidic chip 200) and optical system (detection mechanism 410). The built-in CCD camera was used to capture the fluorescent image of QD on the nanopillar chip (LSPR nanopillar assembly 110) and the emission intensity was analyzed by LabVIEW program. Three pieces of microfluidic chips (fluidic chip 200) were used for each concentration of PCT measurement. The QD emission vs. PCT concentration was plotted in FIG. 16. The POC system is able to measure PCT at 0.5 ng/ml.

Comparison of PCT Detection Using Nanopillars and Nanoholes

Gold nanoholes array on glass (simulated with 140 nm diameter gold nanohole array, with 400 nm pitch and 50 nm of gold) is prepared similar to the nanopillar preparation as herein described. When the light sheds from the top of the gold nanoarray, the plasmonic fields are concentrated at the top and bottom of the gold nanostructures. Gold nanopillars are able to enhance the electromagnetic field at least 24 times, while the gold nanoholes are able to enhance 12 times.

The quantum dot emission on bare glass is 0.4 (arbitrary unit) and on gold film is 4.24±0.07. The three kinds of gold nanoarrays all manifested different level of signal amplification for the bioassay compared with gold surface. The gold nanopillar array on glass presented the highest signal strength of 39.58, followed by gold nanohole array on glass at 12.72 and the gold nanohole array on PMMA at 10.06.

The invention claimed is:

1. A localised surface plasmon resonance (LSPR) nanopillar assembly for use in sensing the presence of a biomarker when attached to a quantum dot, comprising:
   a) a substrate;
   b) an array comprising:
      i) a plurality of metallic LSPR nanopillars, each of the nanopillars consists of a metallic nanopillar body; and
      ii) at least one polymer spacer attached to the nanopillars; and
   c) an antibody attached to the at least one polymer spacer;
   wherein a combined height of the polymer spacer and antibody is such that, when in use with the biomarker and the quantum dot, the quantum dot is in an LSPR region of the nanopillar; and
   each of the at least one polymer spacer comprises a discrete linear or non-linear polymer molecule having at least two opposed terminal ends, a first terminal end being attached to the nanopillar and a second spaced and opposed terminal end being attached to the antibody;
   wherein the polymer spacer is a polyethylene glycol (PEG) spacer;
   wherein the PEG spacer is $PEG_{2-100}$;
   wherein the metallic nanopillar body has a length of about 50 nm to about 250 nm, width of about 50 nm to about 250 nm, and height of about 20 nm to about 100 nm;

wherein the nanopillar array comprises a plurality of metallic nanopillars, in which a pitch of the nanopillar array is about 150 nm to about 500 nm.

2. The LSPR nanopillar assembly of claim 1, wherein the polymer spacer is conjugated to the metallic nanopillar body and the antibody is conjugated to the polymer spacer.

3. The LSPR nanopillar assembly of claim 1, wherein the polymer spacer is maintained in a substantially upright position relative to a surface of the substrate to sense the presence of the biomarker when attached to the quantum dot.

4. The LSPR nanopillar assembly of claim 1, wherein the polymer spacer is conjugated to the nanopillar by a sulphide bond.

5. The LSPR nanopillar assembly of claim 1, wherein the PEG spacer is $PEG_7$.

6. The LSPR nanopillar assembly of claim 1, wherein the metallic nanopillar body has a length of about 140 nm, width of about 140 nm, and height of about 55 nm.

7. The LSPR nanopillar assembly of claim 1, wherein the pitch of the metallic nanopillar array is about 320 nm.

8. The LSPR nanopillar assembly of claim 1, wherein the metallic nanopillar body is substantially wholly made of gold or silver.

* * * * *